(12) United States Patent
Yen

(10) Patent No.: US 10,079,347 B2
(45) Date of Patent: *Sep. 18, 2018

(54) COMPOUNDS FOR ORGANIC ELECTROLUMINESCENCE DEVICE

(71) Applicant: Feng-Wen Yen, Taipei (TW)

(72) Inventor: Feng-Wen Yen, Taipei (TW)

( * ) Notice: Subject to any disclaimer, the term of this patent is extended or adjusted under 35 U.S.C. 154(b) by 412 days.

This patent is subject to a terminal disclaimer.

(21) Appl. No.: 14/745,510

(22) Filed: Jun. 22, 2015

(65) Prior Publication Data

US 2016/0372679 A1 Dec. 22, 2016

(51) Int. Cl.
  *H01L 51/50* (2006.01)
  *H01L 51/00* (2006.01)
  (Continued)

(52) U.S. Cl.
  CPC ........ *H01L 51/0072* (2013.01); *C07D 471/04* (2013.01); *C09K 11/025* (2013.01);
  (Continued)

(58) Field of Classification Search
  None
  See application file for complete search history.

(56) References Cited

U.S. PATENT DOCUMENTS 6,602,618 B2 * 8/2003 Watanabe ........... H01L 51/0081 313/504
8,962,160 B2 2/2015 Yen et al.
(Continued)

FOREIGN PATENT DOCUMENTS

WO 2008062636 A1 5/2008
WO 2012091471 A2 7/2012

*Primary Examiner* — Gregory D Clark

(57) ABSTRACT

The present invention discloses an triphenylene-based fused carbazole compound is represented by the following formula (1) or formula (2), the organic EL device employing the derivative as light emitting host of emitting layer can display good performance like as lower driving voltage and power consumption, increasing efficiency and half-life time.

formula(1)

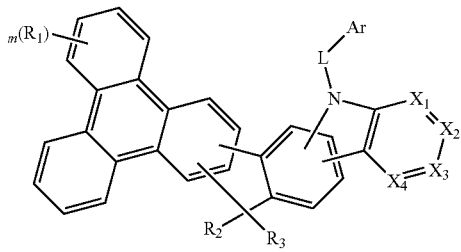

formula(2)

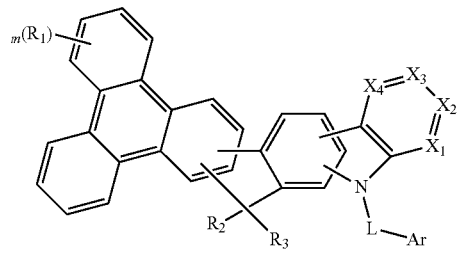

wherein Ar, $X_1$ to $X_4$, m, and $R_1$ to $R_3$ are the same definition as described in the present invention.

19 Claims, 1 Drawing Sheet

| 14 | — metal electrode |
|---|---|
| 13 | — electron injection layer |
| 12 | — electron transport layer |
| 11 | — hole blocking layer |
| 10 | — emitting layer |
| 9 | — electron blocking layer |
| 8 | — hole transport layer |
| 7 | — hole injection layer |
| 6 | — transparent electrode |

(51) Int. Cl.

| | |
|---|---|
| *C07D 471/04* | (2006.01) |
| *C09K 11/06* | (2006.01) |
| *C09K 11/02* | (2006.01) |
| *H05B 33/14* | (2006.01) |
| *H05B 33/20* | (2006.01) |

(52) U.S. Cl.
   CPC .......... *C09K 11/06* (2013.01); *H01L 51/0067* (2013.01); *H05B 33/14* (2013.01); *H05B 33/20* (2013.01); *C09K 2211/1007* (2013.01); *C09K 2211/1029* (2013.01); *C09K 2211/1044* (2013.01); *C09K 2211/1059* (2013.01); *H01L 51/0085* (2013.01); *H01L 51/5012* (2013.01); *H01L 51/5016* (2013.01)

(56) References Cited

U.S. PATENT DOCUMENTS

| | | | |
|---|---|---|---|
| 8,993,130 | B2 | 3/2015 | Yen et al. |
| 2007/0170424 | A1* | 7/2007 | Nishita ............... H01L 51/5096 257/40 |
| 2013/0048975 | A1 | 2/2013 | Hong et al. |
| 2014/0151645 | A1 | 6/2014 | Yen et al. |
| 2014/0166988 | A1* | 6/2014 | Yen .................... H01L 51/0058 257/40 |
| 2014/0175383 | A1 | 6/2014 | Yen et al. |
| 2014/0209866 | A1 | 7/2014 | Yen et al. |
| 2014/0231754 | A1 | 8/2014 | Yen et al. |

\* cited by examiner

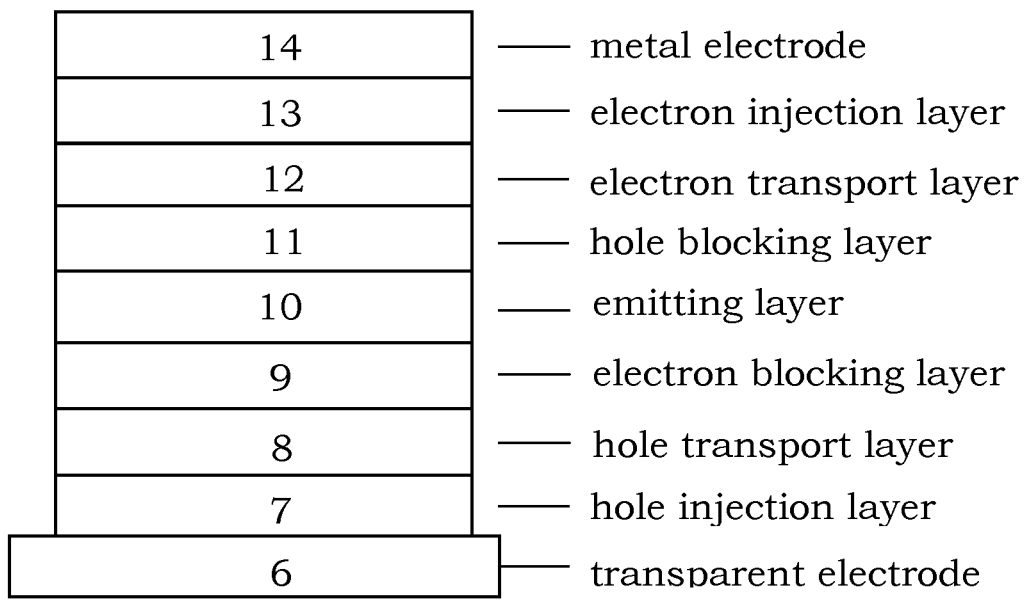

COMPOUNDS FOR ORGANIC ELECTROLUMINESCENCE DEVICE

FIELD OF INVENTION

The present invention generally relates to a triphenylene-based fused carbazole compound and organic electroluminescence (herein referred to as organic EL) device using the compound. More specifically, the present invention relates to the compound having general formula (1) or formula (2), an organic EL device employing the compound as phosphorescent light emitting host of emitting layer or a thermally activated delayed fluorescence (TADF) material of emitting layer.

BACKGROUND OF THE INVENTION

Organic electroluminescence (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

Recently, a new type of fluorescent organic EL incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC).

For full-colored flat panel displays in AMOLED or OLED lighting panel the material used for the phosphorescent host for emitting layer are still unsatisfactory in half-lifetime, efficiency and driving voltage for industrial practice use.

SUMMARY OF THE INVENTION

According to the reasons described above, the present invention has the objective of resolving such problems of the prior-art and offering a light emitting device which is excellent in its thermal stability, high luminance efficiency, high luminance and long half-life time. The present invention disclose a compound having general formula (1) or formula (2), used as a phosphorescent light emitting host of emitting layer or a thermally activated delayed fluorescence (TADF) material of emitting layer have good charge carrier mobility and excellent operational durability can lower driving voltage and power consumption, increasing efficiency and half-life time of organic EL device.

The present invention has the economic advantages for industrial practice. Accordingly, the present invention discloses the compound which can be used for organic EL device is disclosed. The mentioned the compound is represented by the following formula (1) or formula (2):

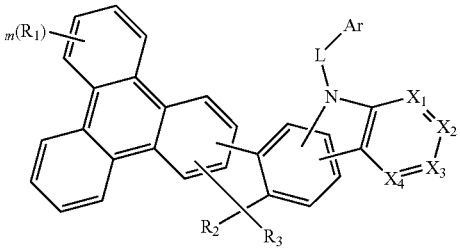

formula(1)

3

-continued

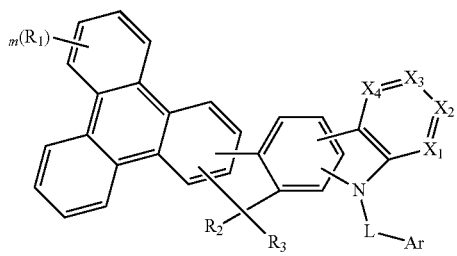

formula(2)

wherein L represents a single bond, a substituted or unsubstituted arylene group having 6 to 30 ring carbon atoms, or a substituted or unsubstituted heterarylene group having 3 to 30 ring carbon atoms, Ar is selected from the group consisting of a substituted or unsubstituted aryl group having 6 to 60 carbon atoms or a substituted or unsubstituted heteroaryl group having 3 to 60 carbon atoms, preferably Ar represents a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $X_1$ to $X_4$ independently represent a nitrogen atom or $C(R_s)$, and each $R_s$ represents a hydrogen, a halide and a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

BRIEF DESCRIPTION OF THE DRAWINGS

FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescent or phosphorescent emitting layer which is deposited onto 9, 11 is hole blocking layer which is deposited onto 10, 12 is electron transport layer which is deposited on to 11, and 13 is electron injection layer which is deposited on to 12.

DESCRIPTION OF THE PREFERRED EMBODIMENTS

What probed into the invention is the triphenylene-based fused carbazole compound for organic EL device using the compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims In a first embodiment of the present invention, the triphenylene-based fused carbazole compound which can be used as phosphorescent light emitting host of emitting layer or a thermally activated delayed fluorescence (TADF) material of emitting layer for organic EL device are disclosed. The mentioned the triphenylene-based fused carbazole compound represented by the following formula (1) or formula (2):

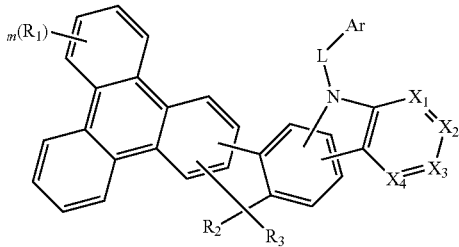

formula(1)

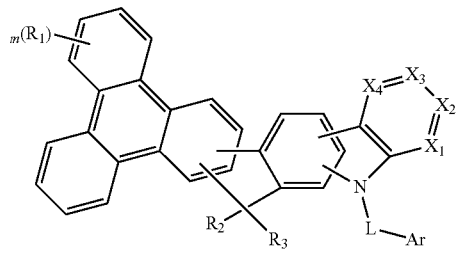

formula(2)

wherein L represents a single bond, a substituted or unsubstituted arylene group having 6 to 30 ring carbon atoms, or a substituted or unsubstituted heterarylene group having 3 to 30 ring carbon atoms, Ar is selected from the group consisting of a substituted or unsubstituted aryl group having 6 to 60 carbon atoms or a substituted or unsubstituted heteroaryl group having 3 to 60 carbon atoms, preferably Ar represents a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $X_1$ to $X_4$ independently represent a nitrogen atom or $C(R_s)$, and each $R_s$ represents a hydrogen, a halide and a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

According to the above-mentioned the triphenylene-based fused carbazole compound formula (1) or formula (2), wherein the L is represented by the following formula (3):

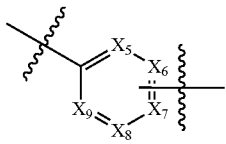

formula(3)

wherein $X_5$ to $X_9$ independently represent a nitrogen atom or $C(R_s)$, and each $R_s$ represents a hydrogen, a phenyl or a substituent.

According to the above-mentioned the triphenylene-based fused carbazole compound formula (1) or formula (2) represented by the following formula (4) to formula (21):

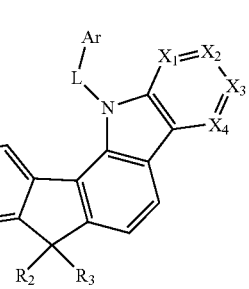

formula(4)

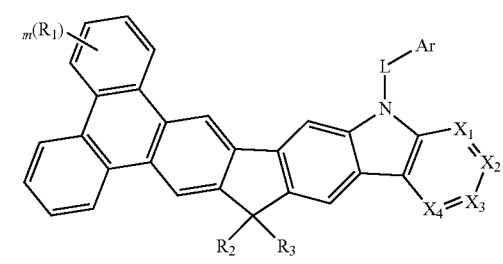

formula(5)

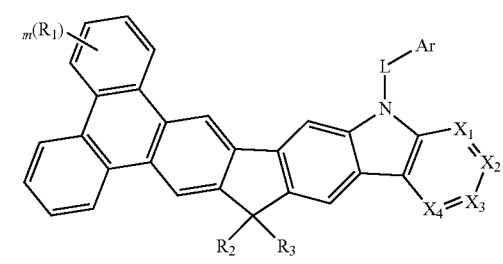

formula(6)

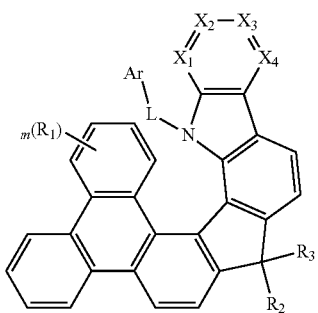

formula(7)

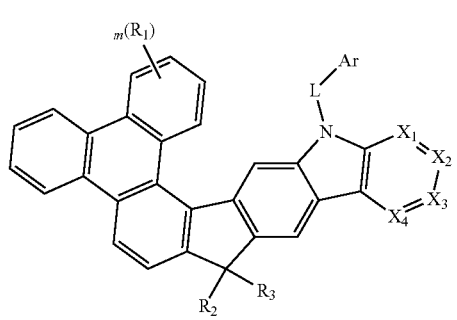

formula(8)

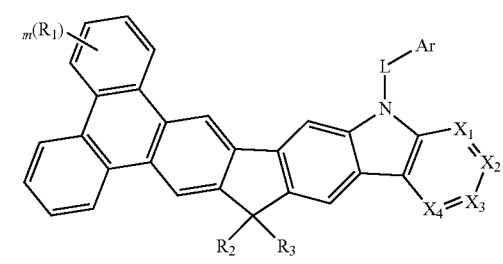

formula(9)

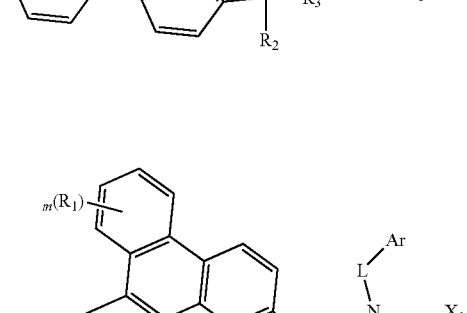

formula(10)

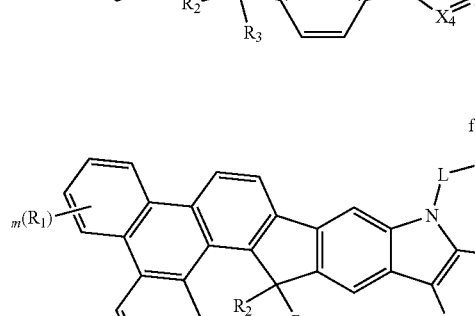

formula(11)

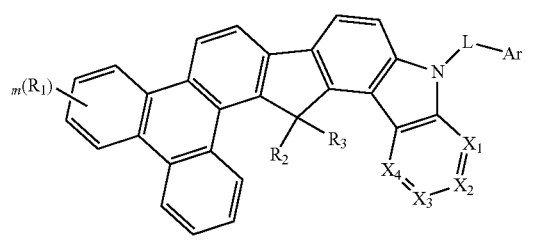
formula(12)

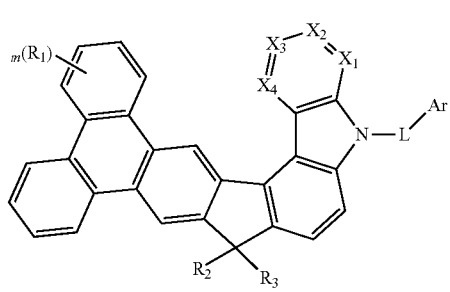
formula(13)

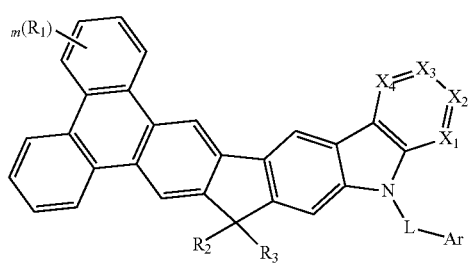
formula(14)

formula(15)

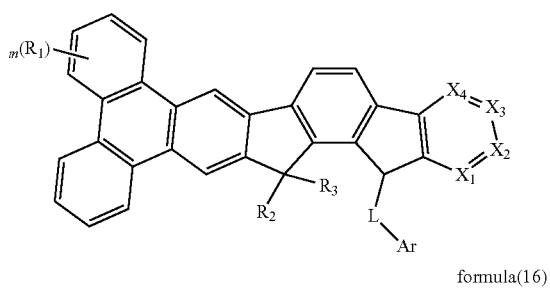

formula(16)

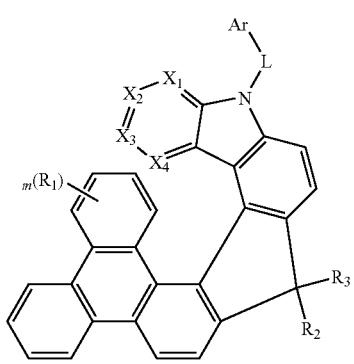

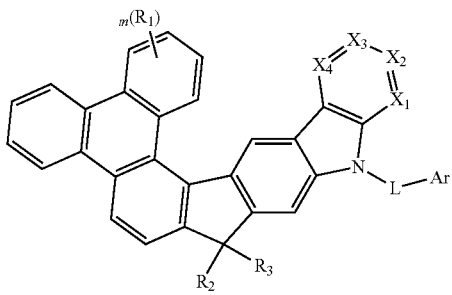
formula(17)

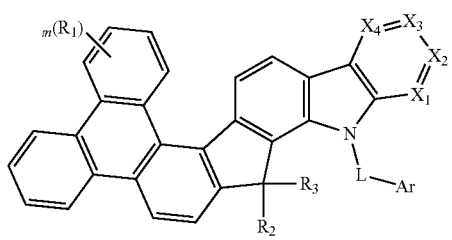
formula(18)

formula(19)

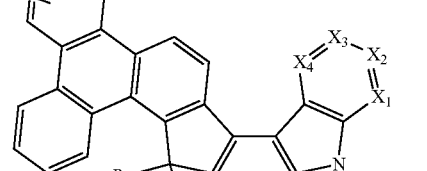

formula(20)

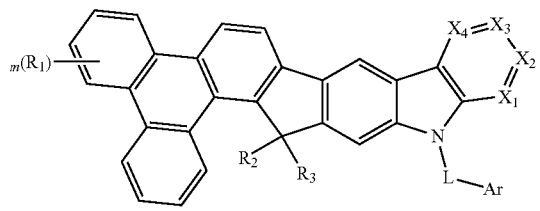

formula(21)

wherein L represents a single bond, a substituted or unsubstituted arylene group having 6 to 30 ring carbon atoms, or a substituted or unsubstituted hetarylene group having 3 to 30 ring carbon atoms, Ar is selected from the group consisting of a substituted or unsubstituted aryl group having 6 to 60 carbon atoms or a substituted or unsubstituted heteroaryl group having 3 to 60 carbon atoms, preferably Ar represents a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $X_1$ to $X_4$ independently represent a nitrogen atom or $C(R_s)$, and each $R_s$ represents a hydrogen, a halide and a substituted, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

According to the above-mentioned the triphenylene-based fused carbazole compound formula (4) or formula (21), wherein the L is represented by the following formula (3):

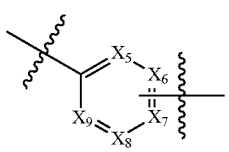

formula(3)

wherein $X_5$ to $X_9$ independently represent a nitrogen atom or $C(R_s)$, and each $R_s$ represents a hydrogen, a phenyl or a substituent.

According to the above-mentioned the triphenylene-based fused carbazole compound formula (4) or formula (21), wherein preferably the Ar is consisting of group represented as follows:

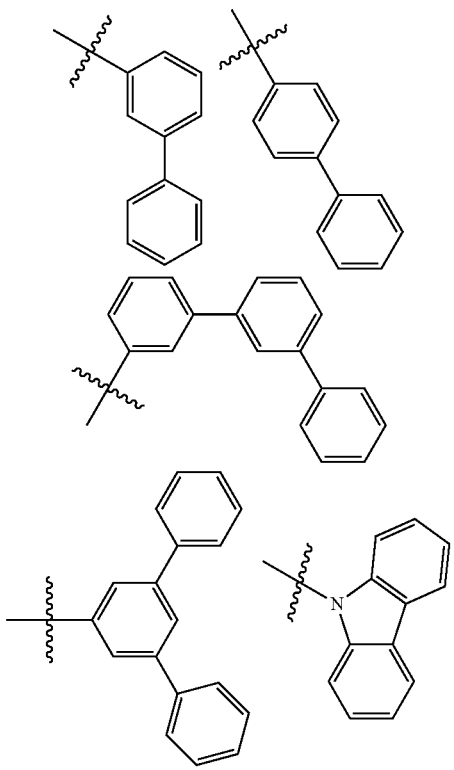

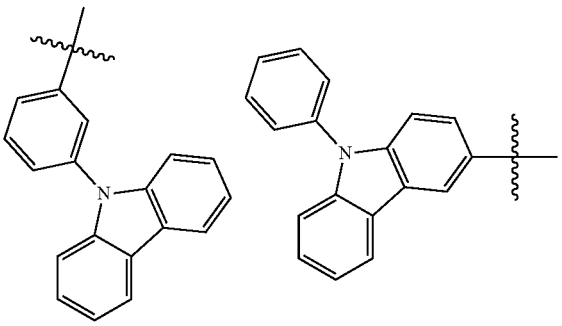

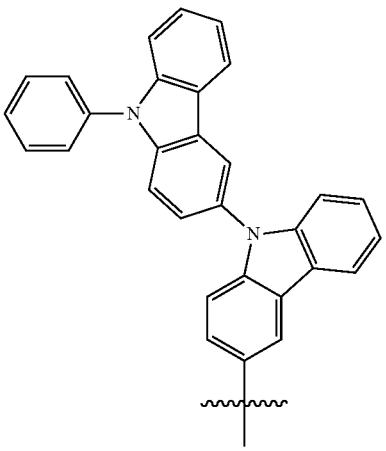

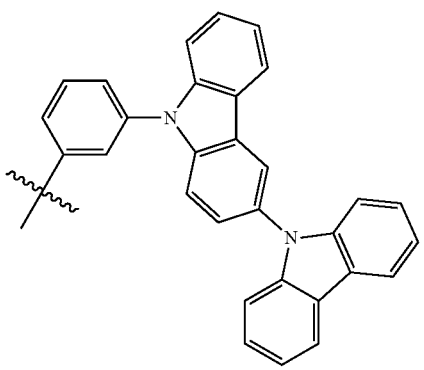

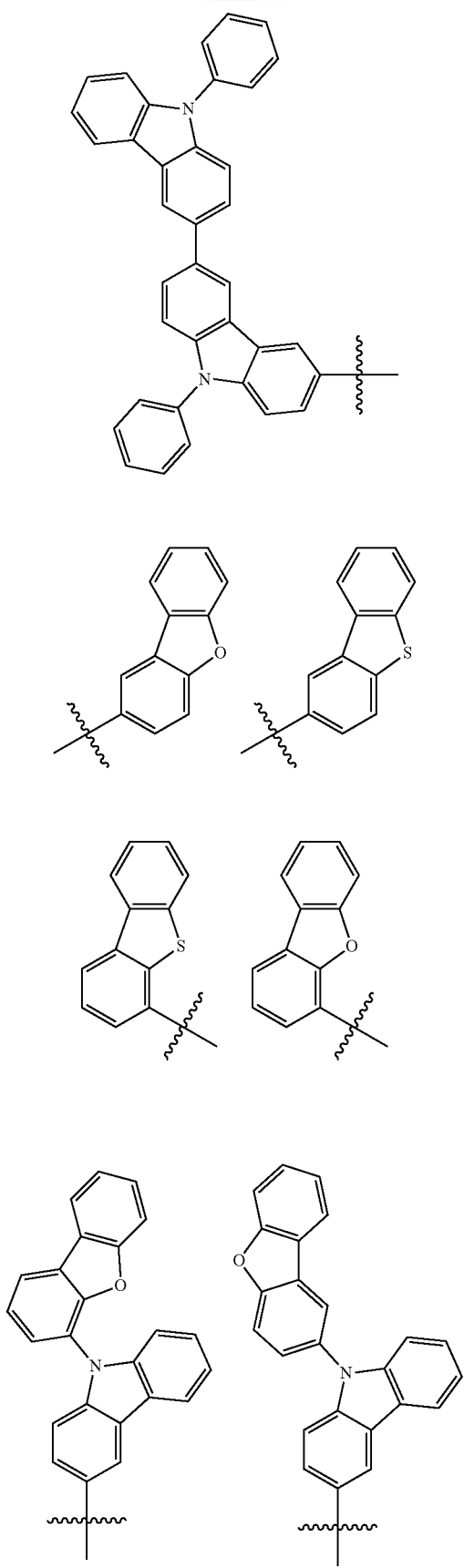

-continued
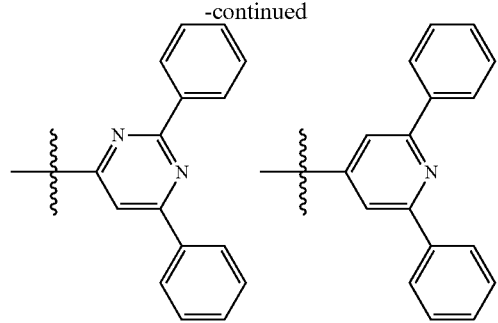
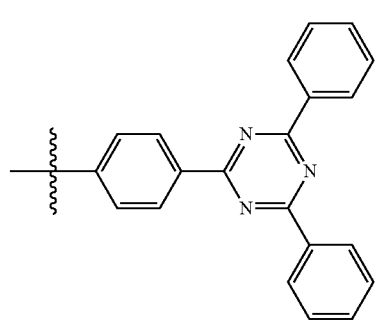
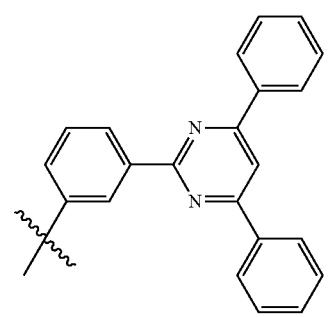
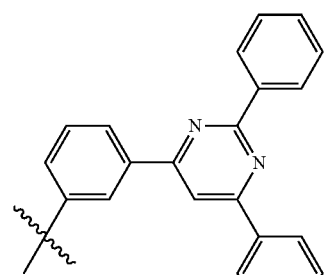
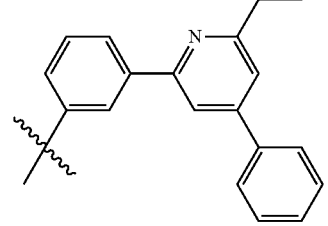
-continued
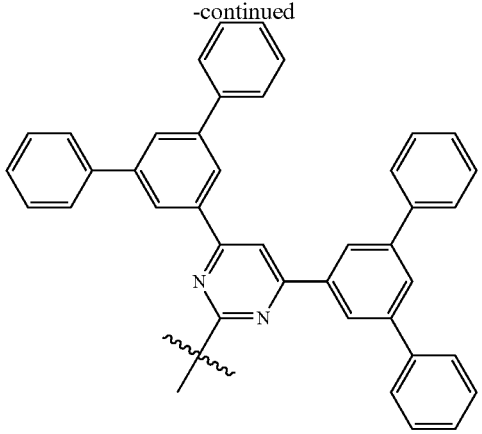
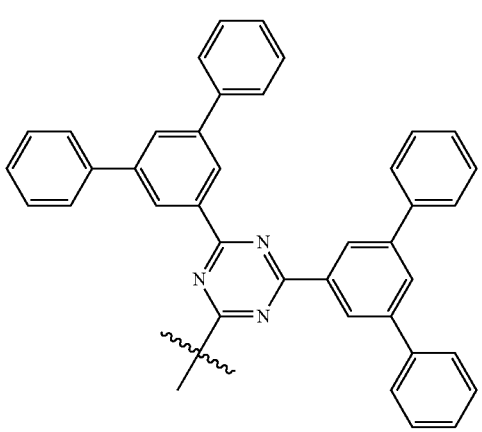
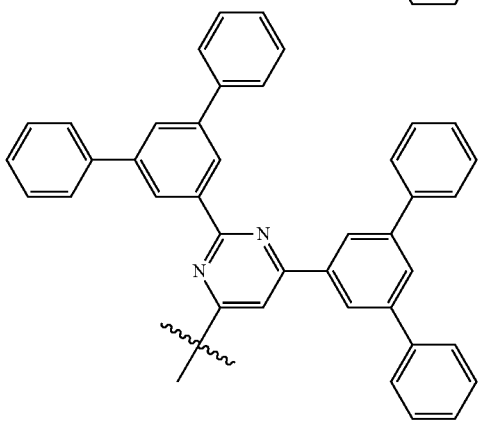
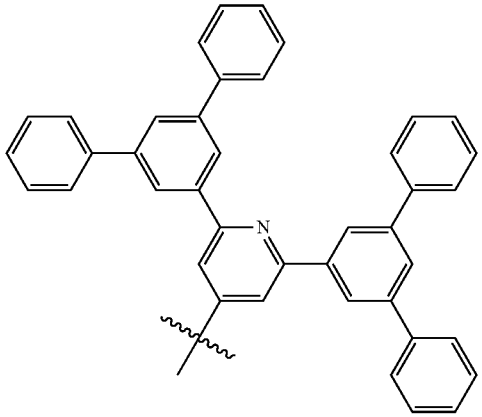

-continued
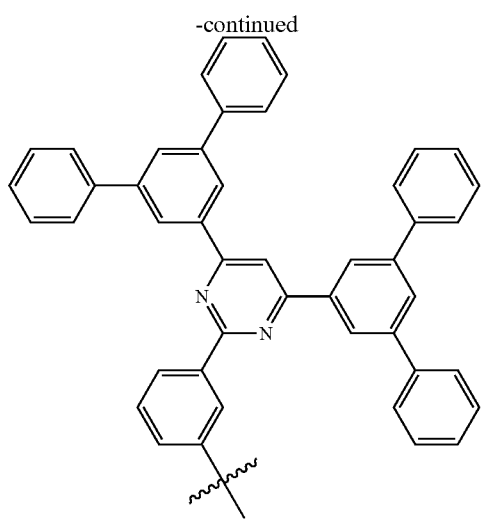
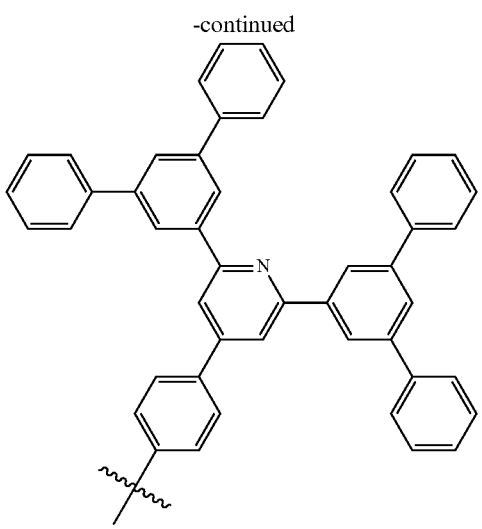
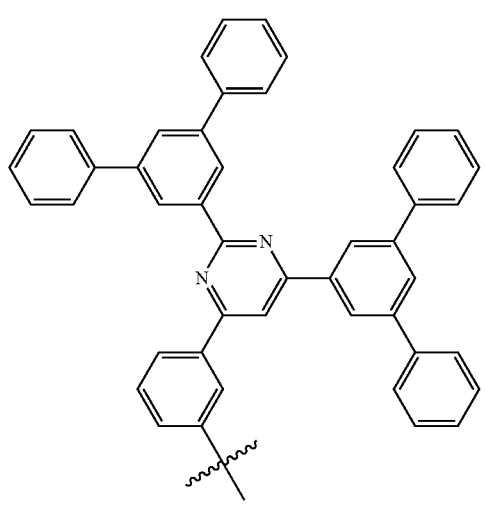
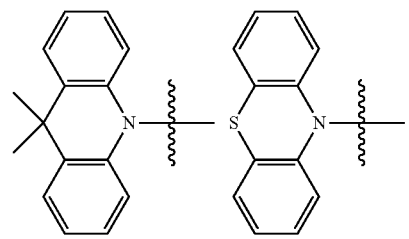
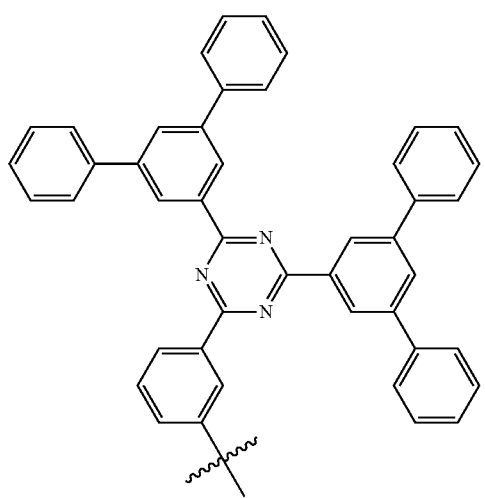
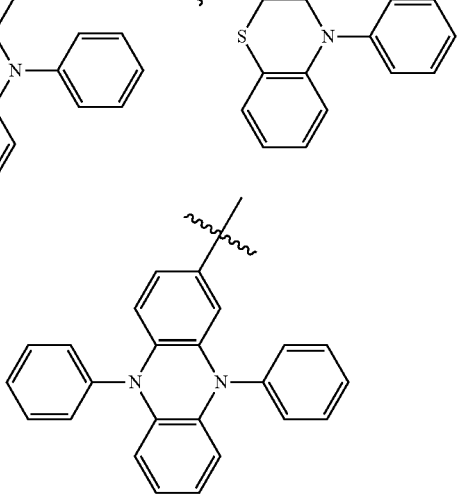

-continued
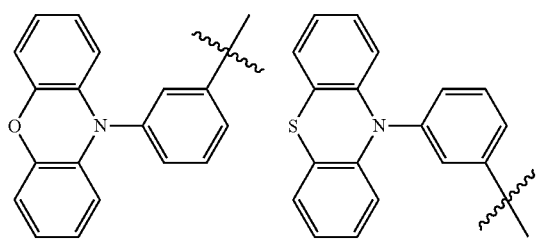
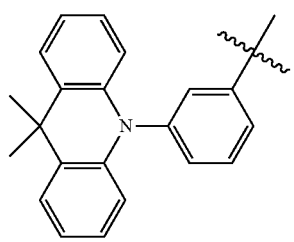
In this embodiment, some triphenylene-based fused carbazole compounds are shown below:
EX1
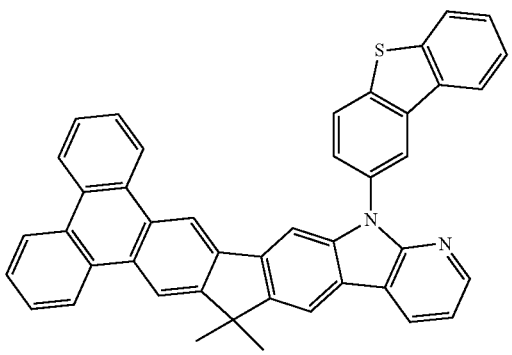
EX2
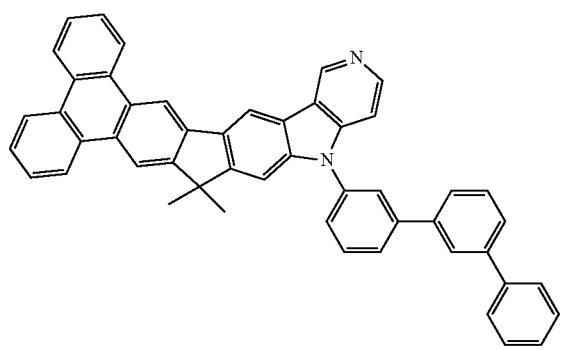
-continued
EX3
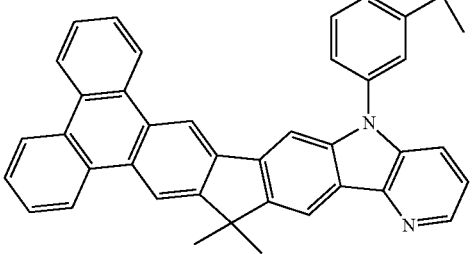
EX4
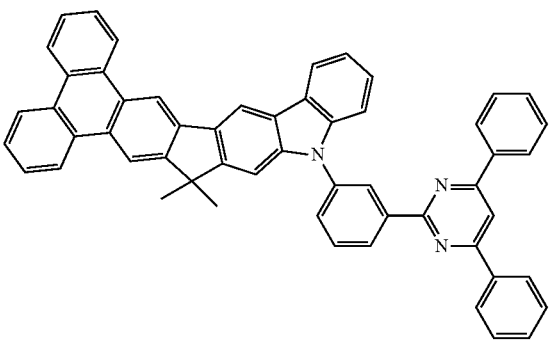
EX5
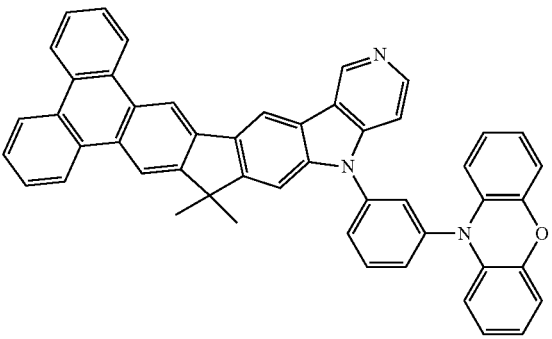
EX6
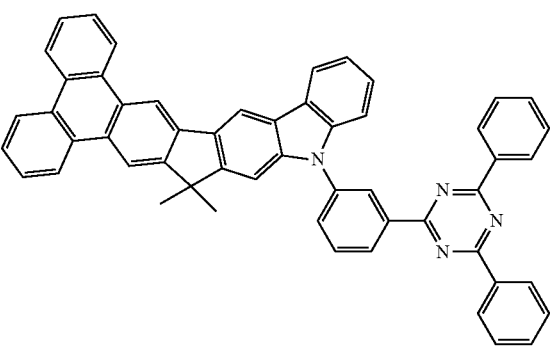

-continued
EX7
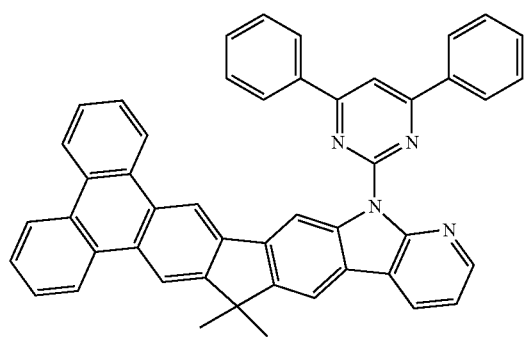
EX8
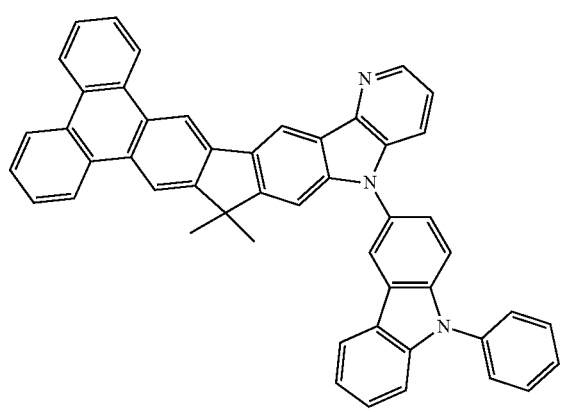
EX9
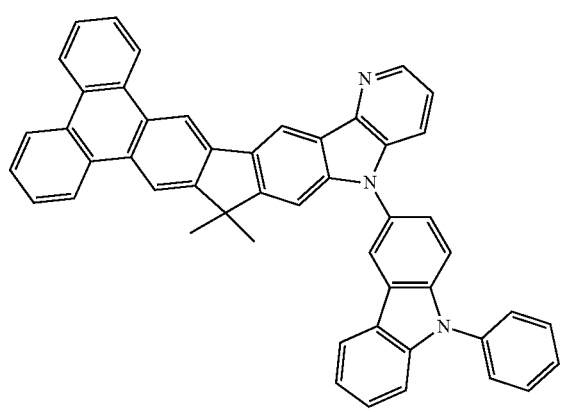
EX10
-continued
EX11
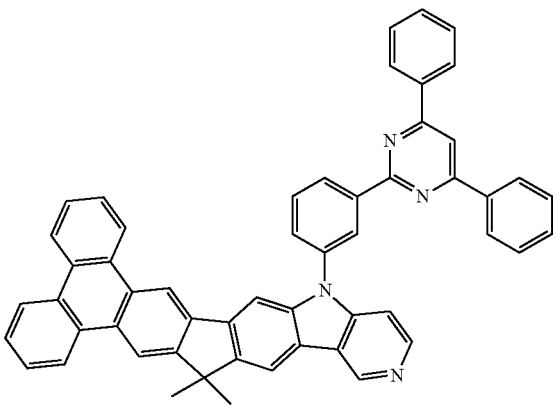
EX12
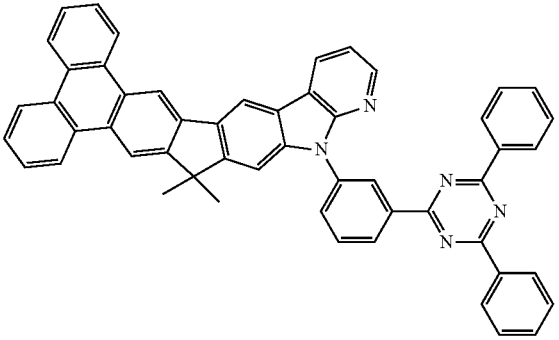
EX13
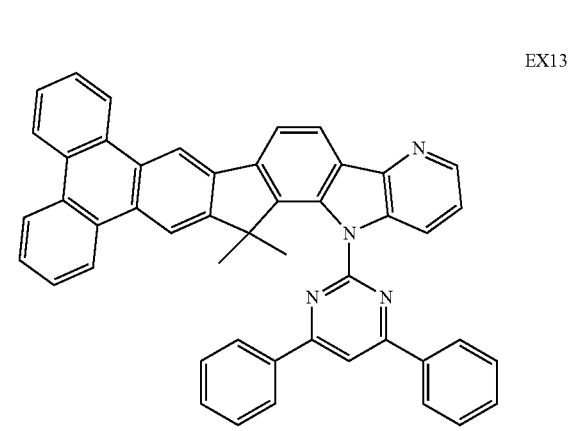
EX14
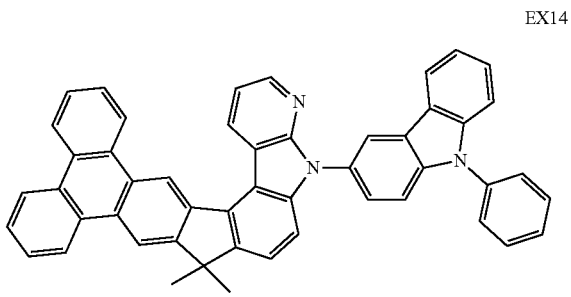

EX15
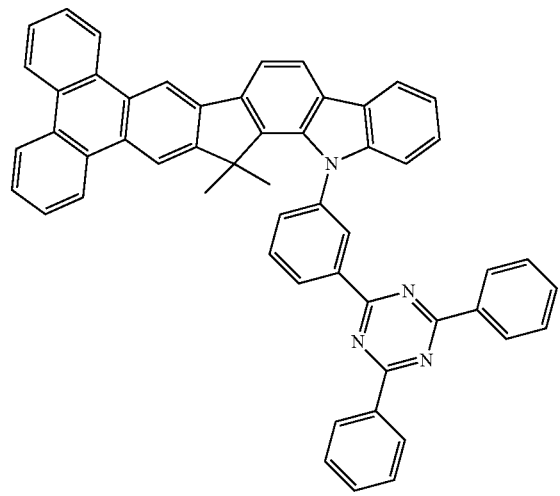
EX16
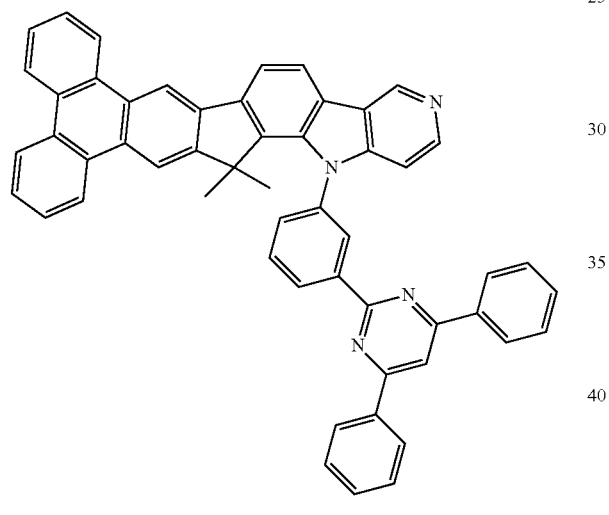
EX17
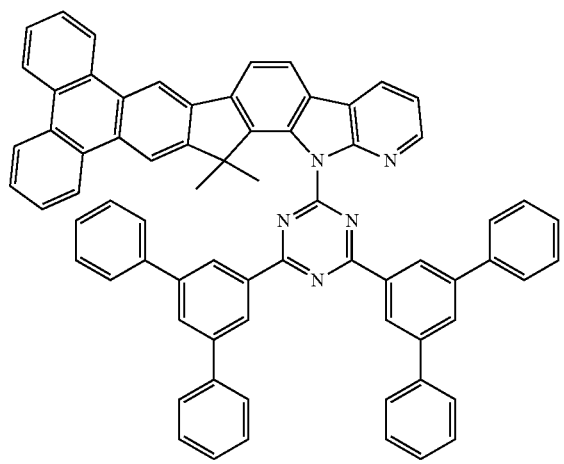
EX18
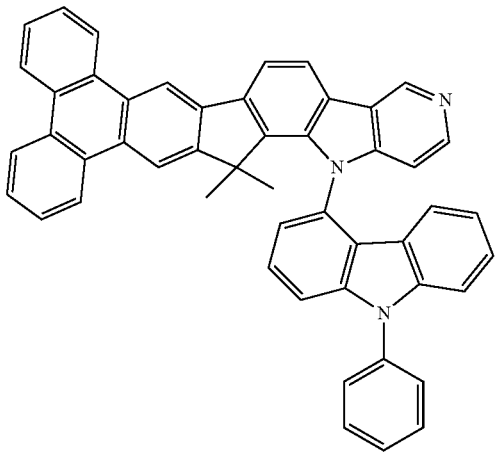
EX19
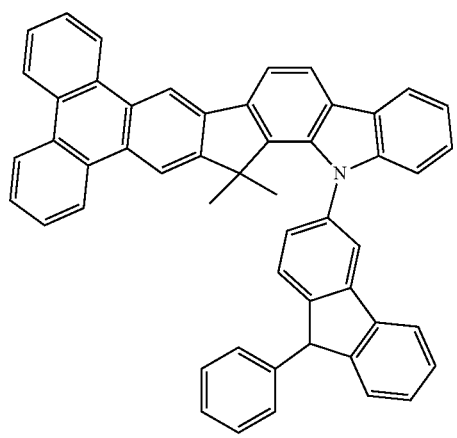
EX20
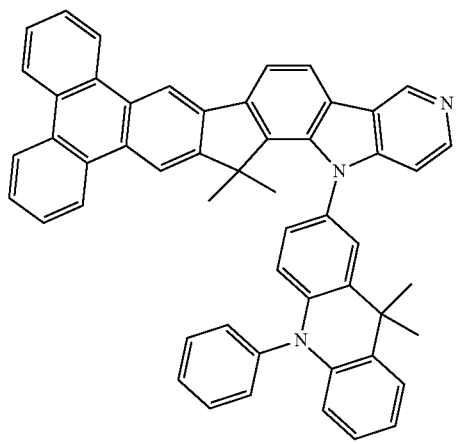

-continued
EX21
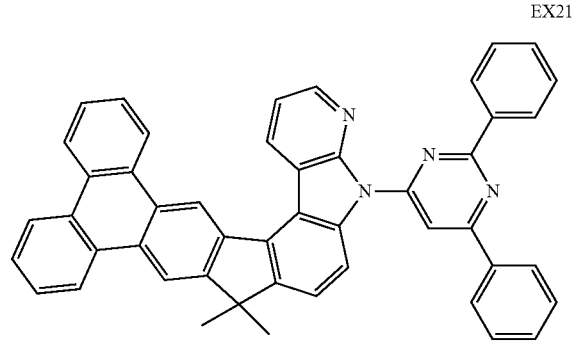
EX22
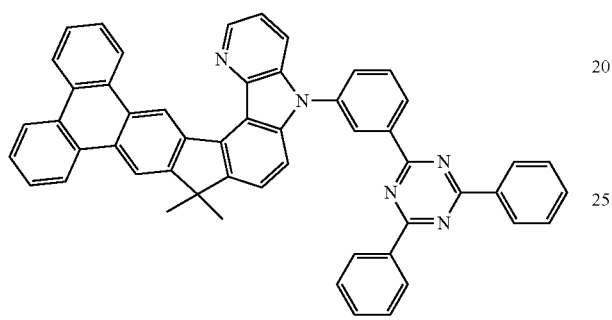
EX23
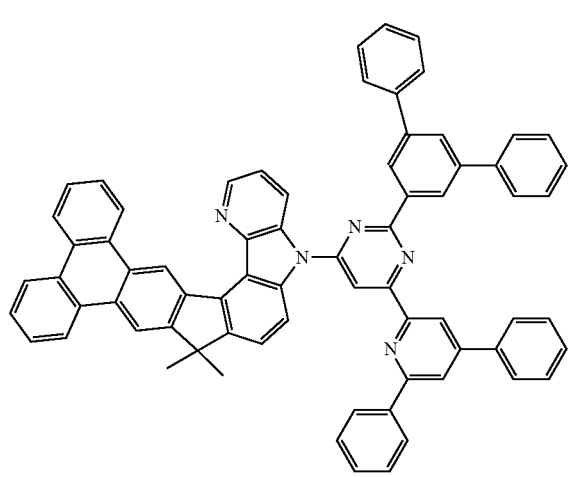
EX24
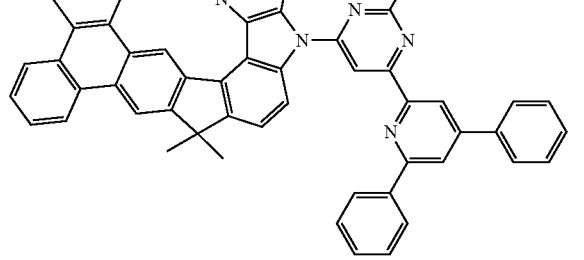
EX25
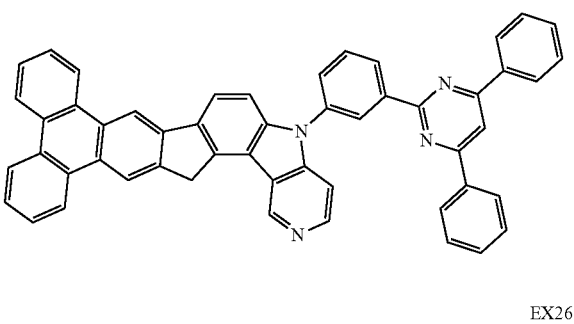
EX26
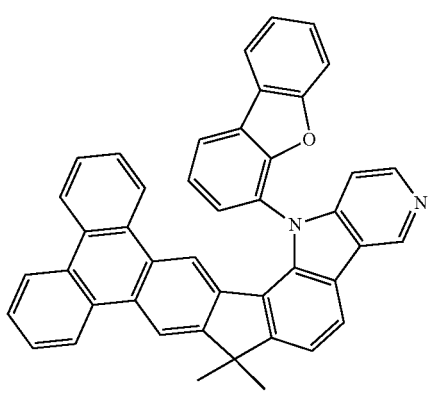
EX27
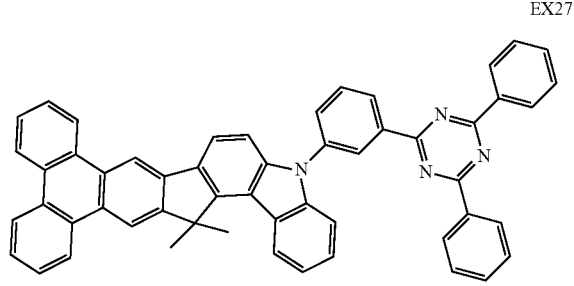
EX28
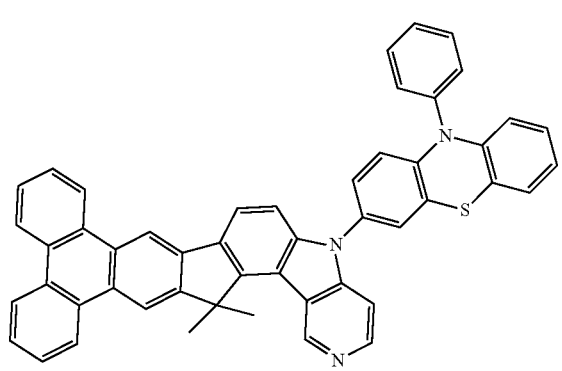
EX29
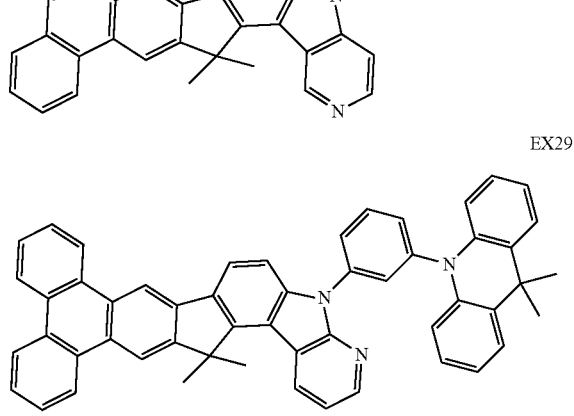

-continued
EX30
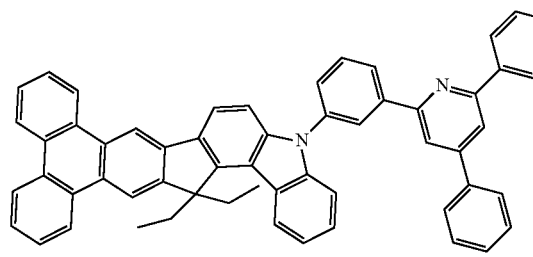
EX31
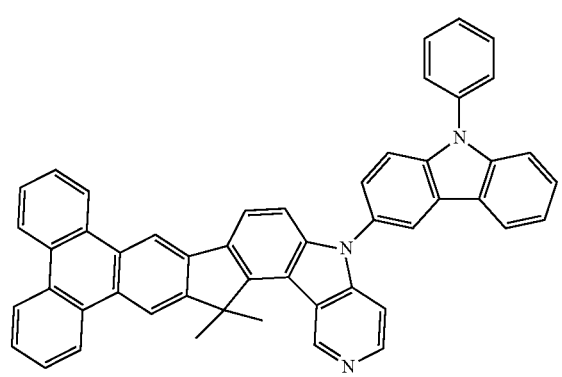
EX32
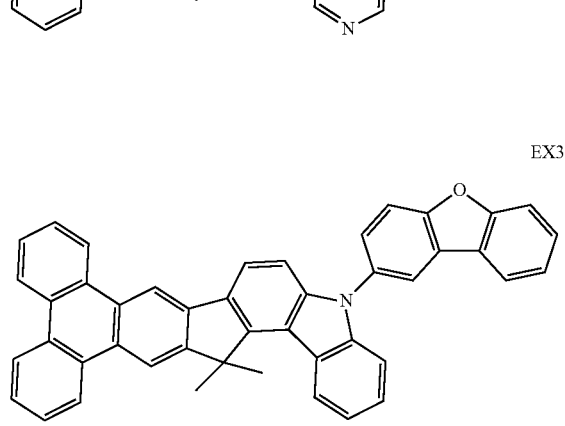
EX33
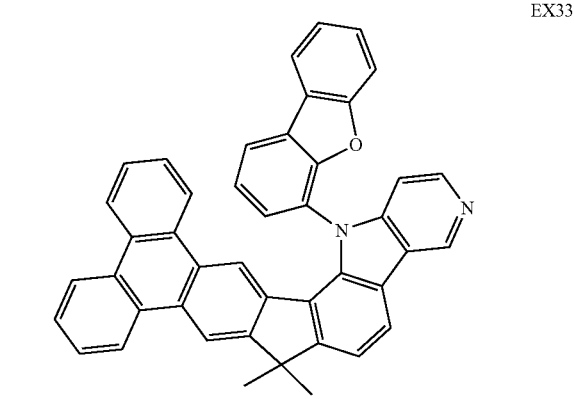
EX34
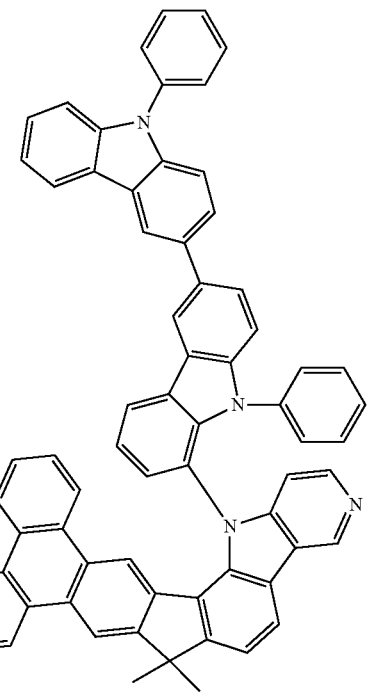
EX35
EX36

EX37
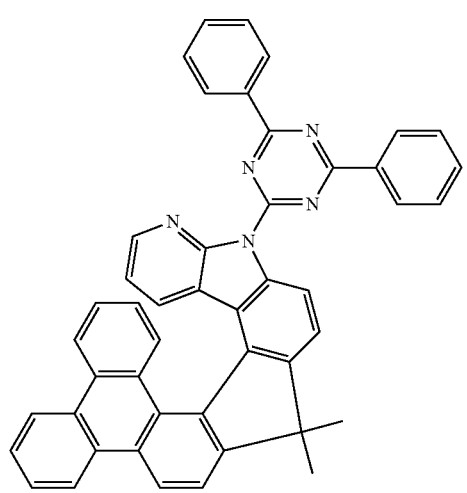
EX40
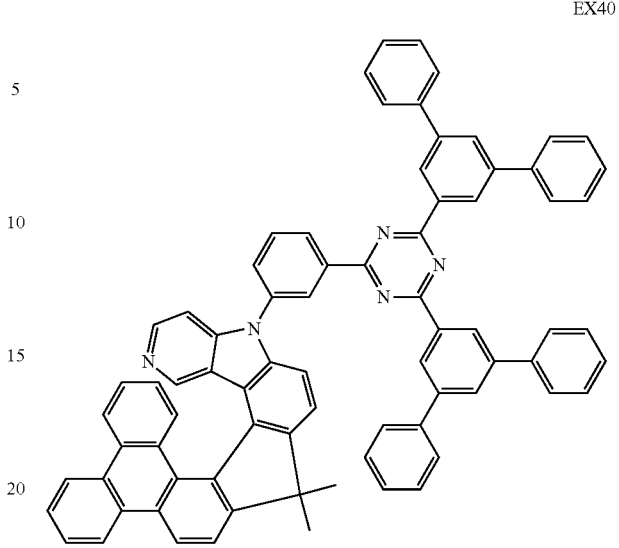
EX38
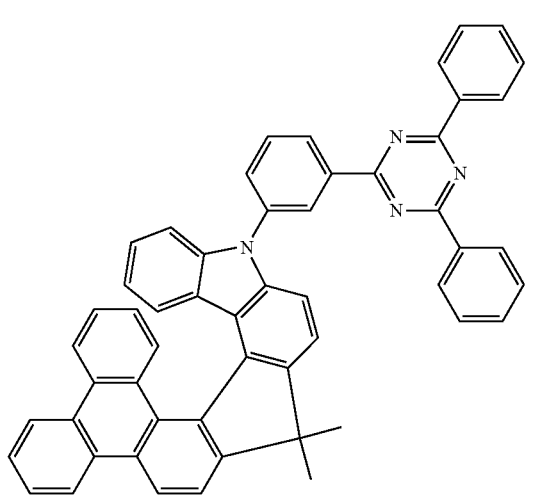
EX41
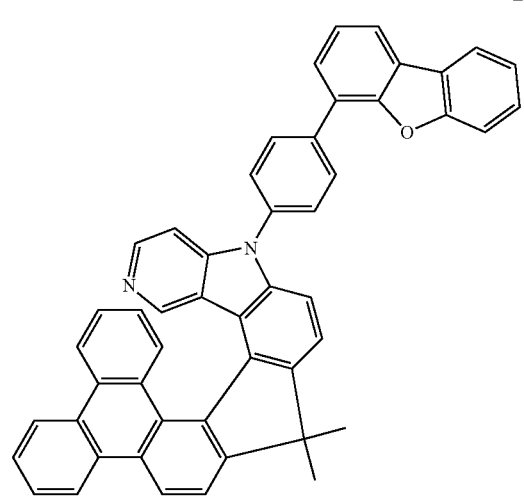
EX39
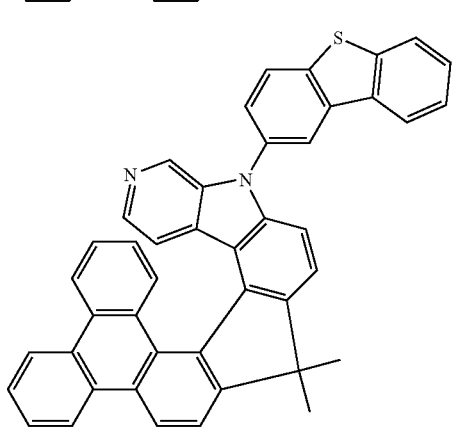
EX42

EX43
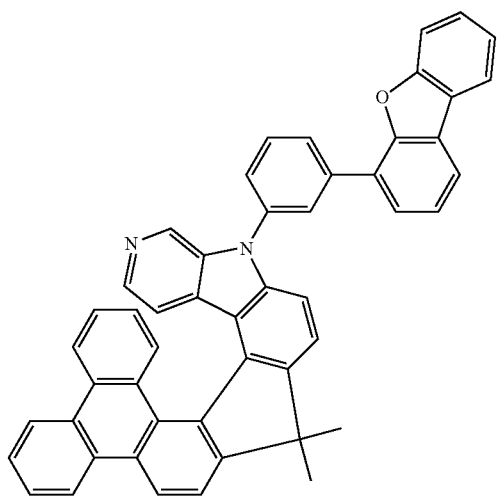
EX44
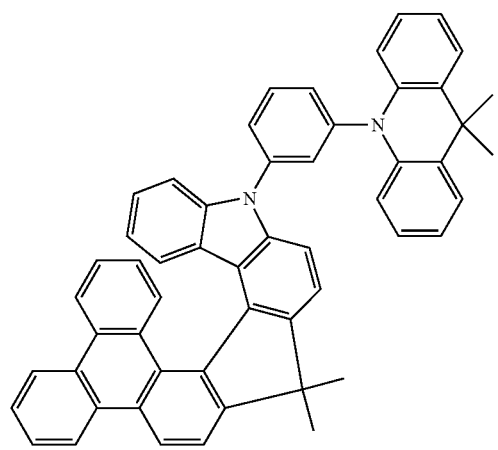
EX45
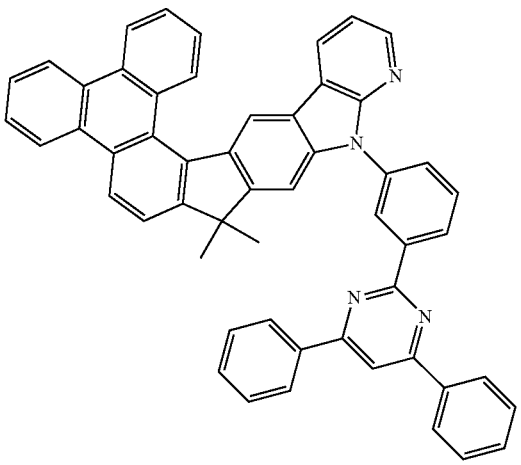
EX46
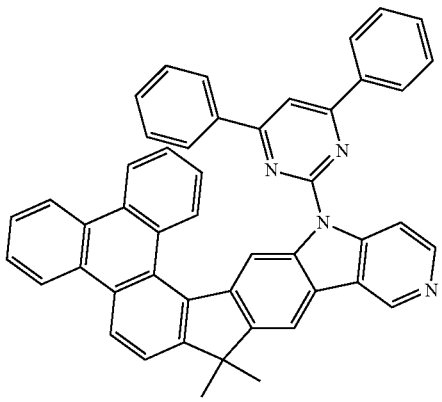
EX47
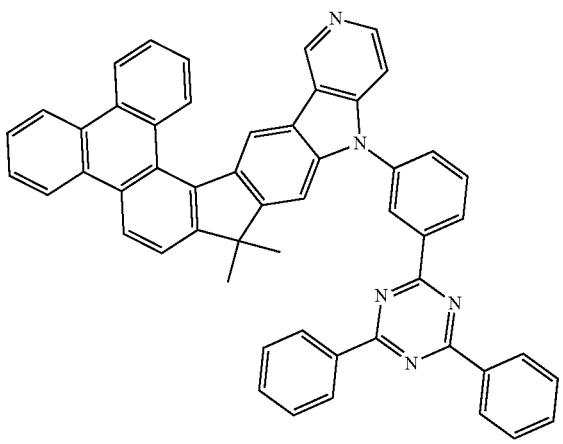
EX48

EX49
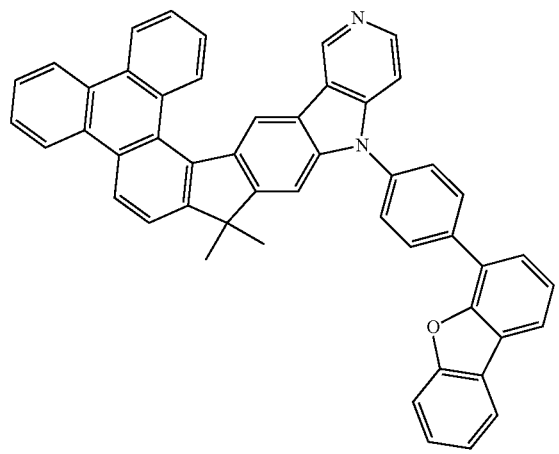
EX50
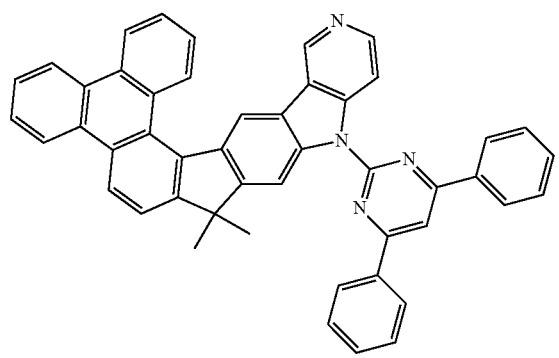
EX51
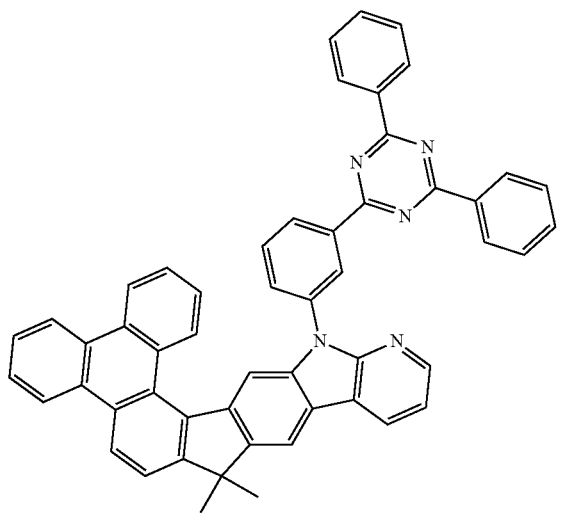
EX52
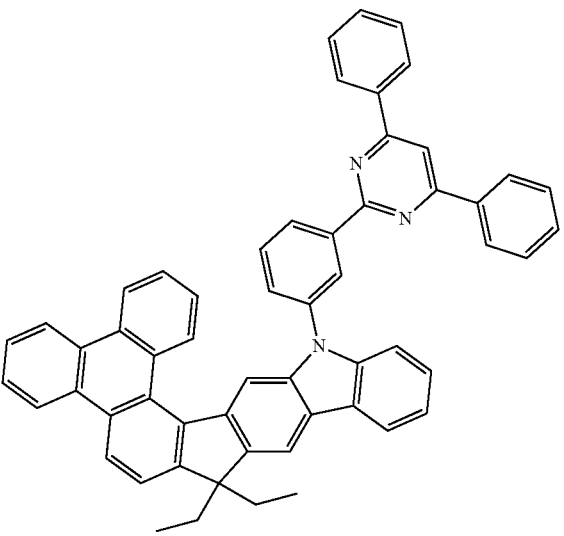
EX53
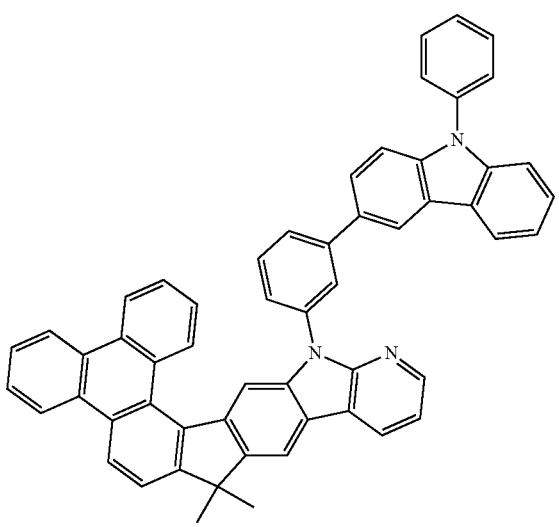
EX54
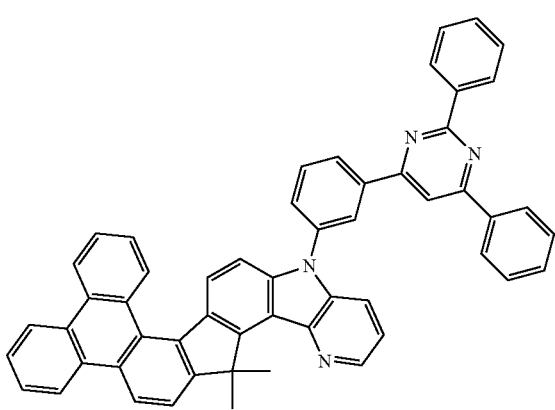

EX55
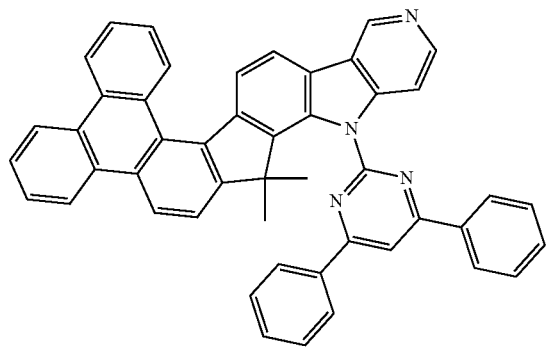
EX56
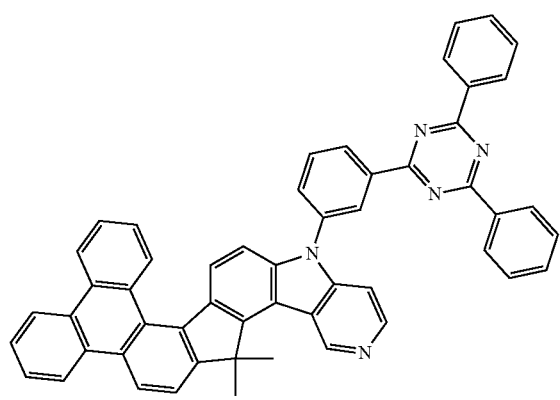
EX57
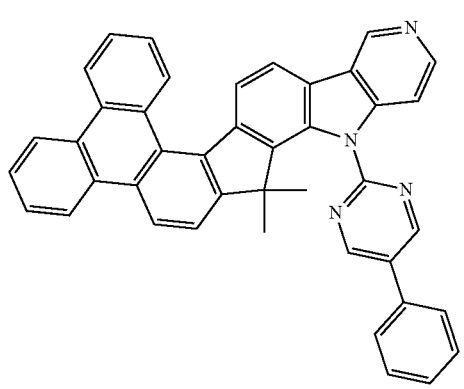
EX58
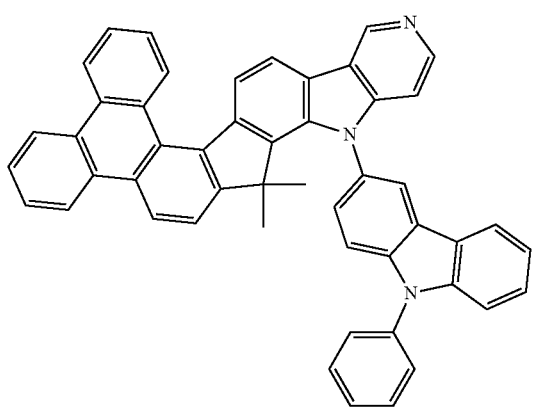
EX59
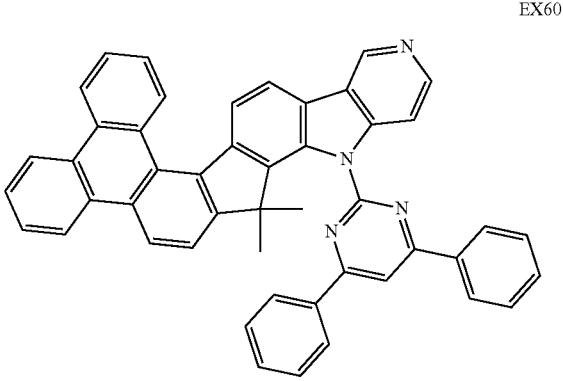
EX60
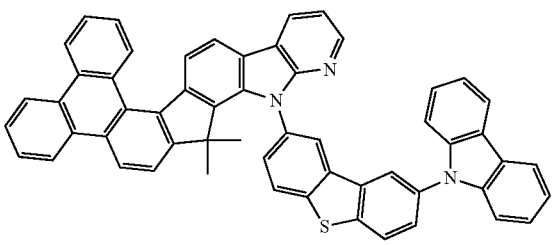
EX61
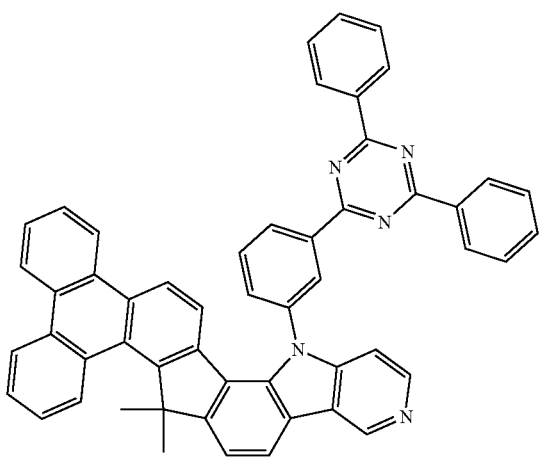
EX62

-continued
EX63
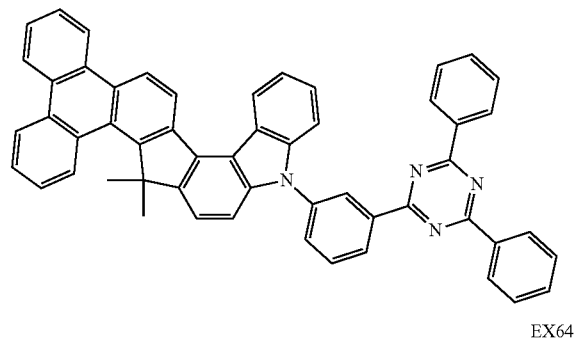
EX64
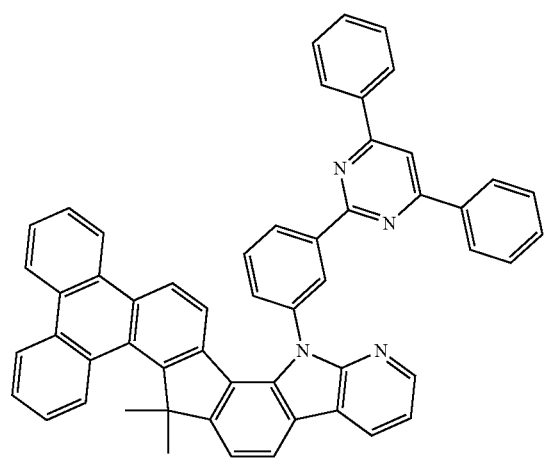
EX65
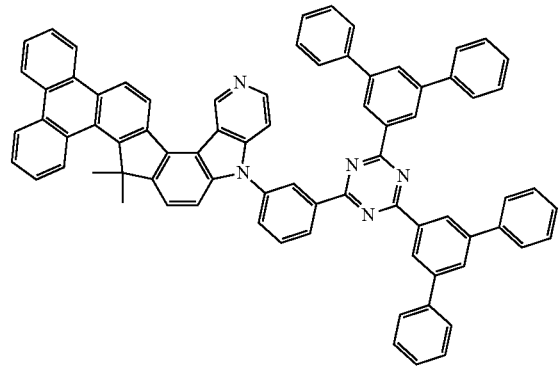
EX66
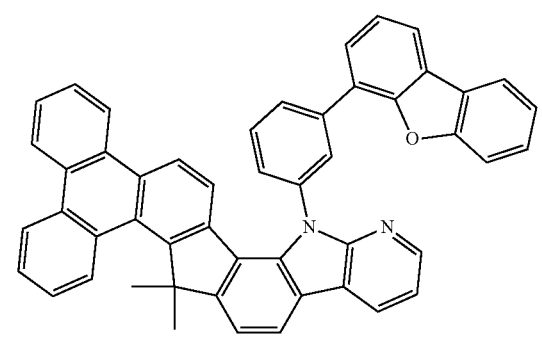
-continued
EX67
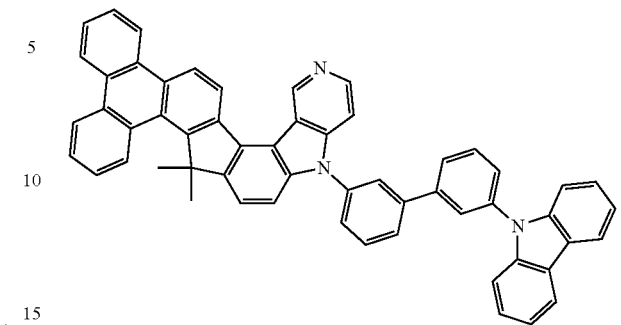
EX68
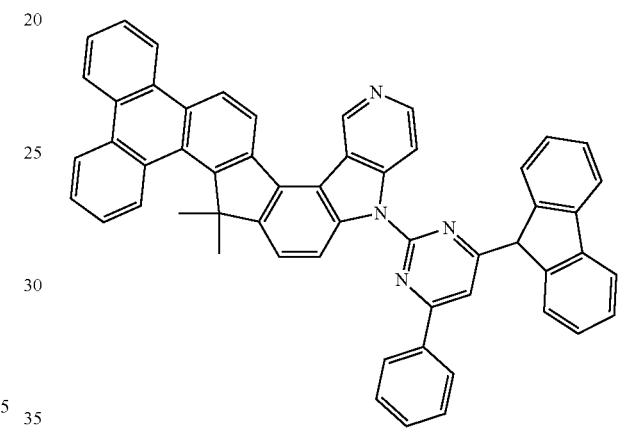
EX69
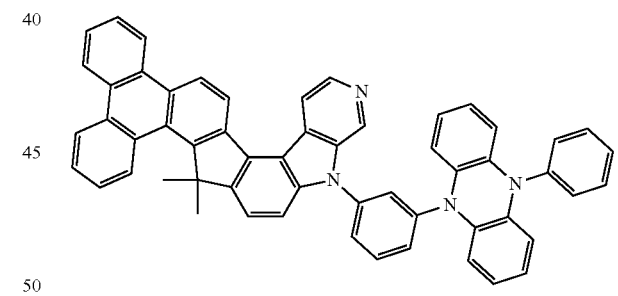
EX70
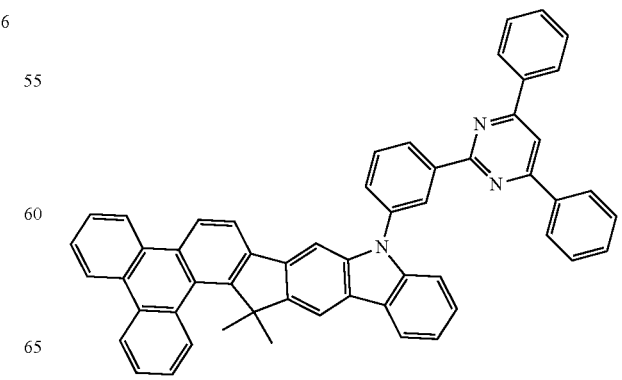

-continued

EX71
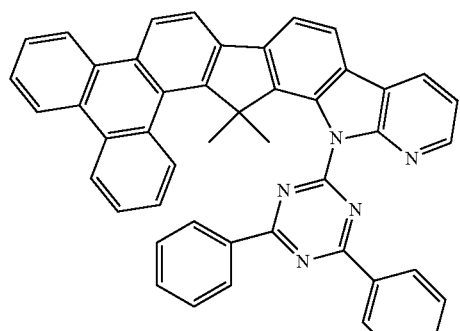

EX72
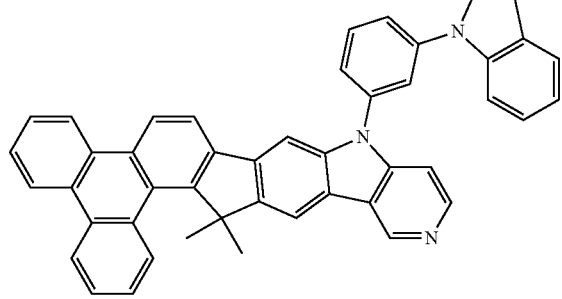

EX73
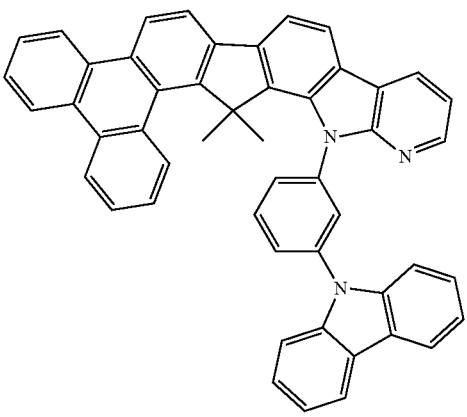

EX74
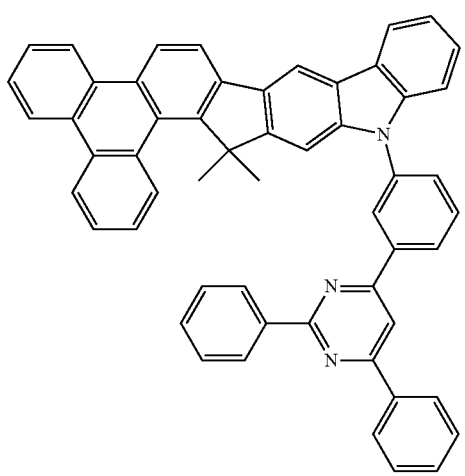

-continued

EX75
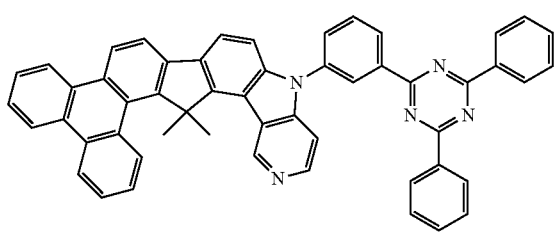

EX76
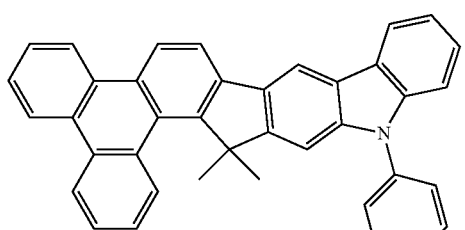

EX77
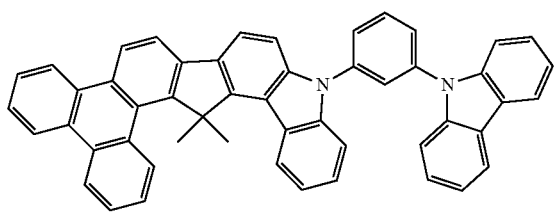

Detailed preparation for the triphenylene-based fused carbazole compound in the present invention could be clarified by exemplary embodiments, but the present invention is not limited to exemplary embodiments. EXAMPLE 1 to EXAMPLE 3 show the preparation for examples of the triphenylene-based fused carbazole compound in the present invention. EXAMPLE 4 shows the fabrication of organic EL device and I-V-B, half-life time of organic EL device testing report.

EXAMPLE 1

Synthesis of EX7

Synthesis of 2-(biphenyl-2-yl)-6-bromo-9,9-dimethyl-9H-fluorene

-continued

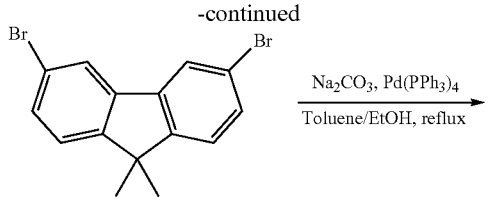

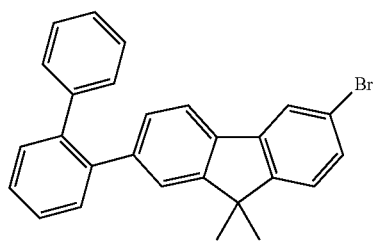

A mixture of 35.2 g (100 mmol) of 3,6-dibromo-9,9-dimethyl-9H-fluorene, 21.8 g (110 mmol) of biphenyl-2-ylboronic acid, 2.31 g (2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica gel to give product (26.8 g, 63.0 mmol, 63%) as a white solid.

Synthesis of 13-bromo-10,10-dimethyl-10H-indeno[2,1-b]triphenylene

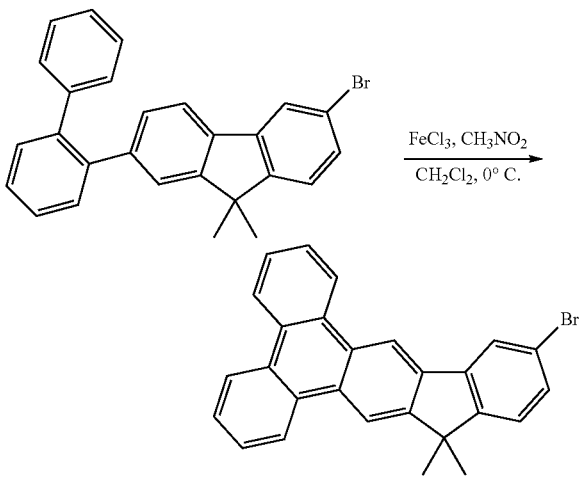

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron(III)chloride was then added, and the mixture was stirred one hour. Methanol 500 ml were added to the mixture and the organic layer was separated, and the solvent removed in vacuo. The residue was purified by column chromatography on silica gel (hexane-dichloromethane) afforded a white solid (10.7 g, 25.3 mmol, 40%). $^1$H NMR (CDCl$_3$, 500 MHz): chemical shift (ppm) 8.93 (s, 1H), 8.77~8.71 (m, 2H), 8.67~8.65 (m, 3H), 8.08 (d, J=1.5 Hz, 1H), 7.71~7.64 (m, 4H), 7.49 (dd, J$_1$=8.5 Hz, J$_2$=1.5 Hz, 1H), 7.37 (d, J=8.5 Hz, 1H), 1.62 (s, 6H).

Synthesis of 3-chloro-N-(10,10-dimethyl-10H-indeno[2,1-b]triphenylen-13-yl)pyridin-2-amine

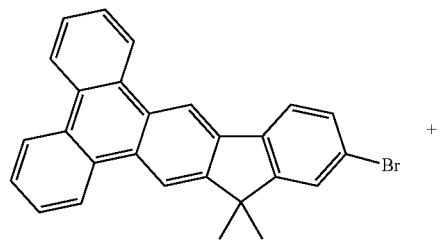

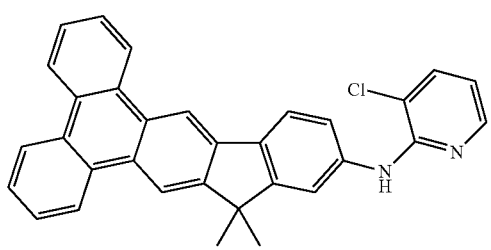

A mixture of 10.7 g (25.3 mmol) of 13-bromo-10,10-dimethyl-10H-indeno-[1,2-b]triphenylene, 3.3 g (25.4 mmol) of 3-chloropyridin-2-amine, 0.11 g (0.5 mmol) of palladium(II)acetate, 0.55 g (1.0 mmol) of 1,1-bis(diphenylphosphino)ferrocene, 4.85 g (50.6 mmol) of sodium tert-butoxide and 100 ml toluene was degassed and placed under nitrogen, and then heated at 110° C. for overnight. After finishing the reaction, the mixture was allowed to cool to room temperature. The organic phase separated and washed with ethyl acetate and water. After drying over magnesium sulfate, the solvent was removed in vacuo. The residue was purified by column chromatography on silica gel (hexane-dichloromethane) to give product (7.5 g, 15.9 mmol, 63%).

Synthesis of intermediate I

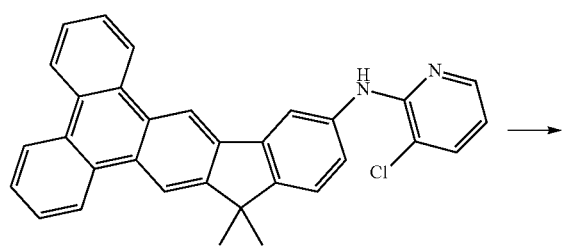

-continued

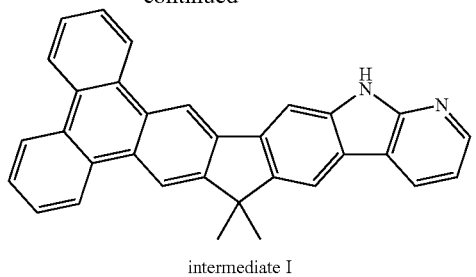

intermediate I

A mixture of 6.9 g (14.7 mmol) of 3-chloro-N-(10,10-dimethyl-10H-indeno[2,1-b]triphenylen-13-yl)pyridin-2-amine, 0.4 g (1.6 mmol) of palladium(II) acetate, 70 ml of pivalic acid, 0.72 g of potassium carbonate (6 mmol) and 210 ml 1-methyl-2-pyrrolidone was degassed and placed under nitrogen, and then heated at 130° C. for 24 hours. After finishing the reaction, the mixture was allowed to cool to room temperature. The organic layer was extracted with dichloromethane and water, dried with anhydrous magnesium sulfate, the solvent was removed and the residue was recrystallized from hexane and dichloromethane to give product 5.0 g (yield 78%).

Synthesis of EX7

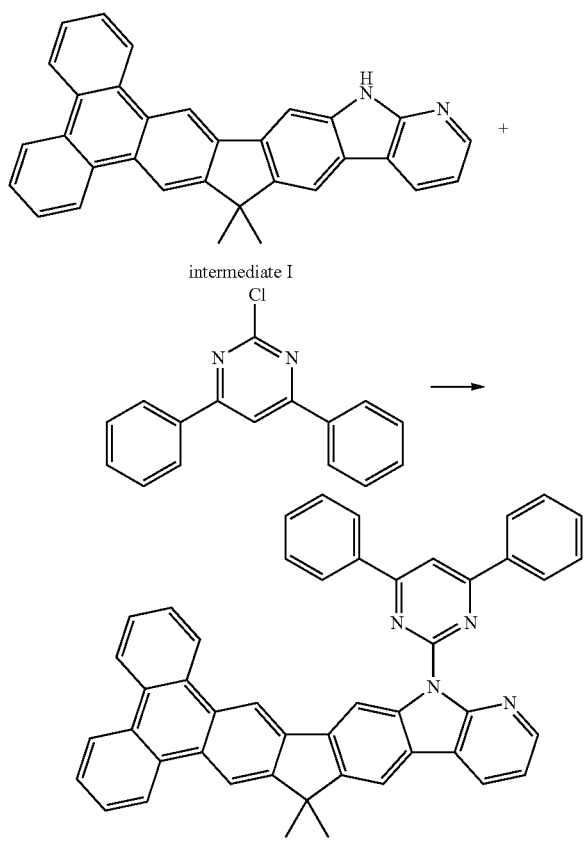

Under $N_2$ condition, 5 g (11.5 mmol) of intermediate I and 100 ml of DMF were mixed, and 1.1 g (46 mmol) of NaH was slowly added to the mixture. The mixture was stirred at room temperature for 30 minutes, then 4 g (15 mmol) of 2-chloro-4,6-diphenylpyrimidine was slowly added to the mixture. The mixture was stirred at room temperature for 24 hours. After completion of the reaction, 300 ml of iced water was added, while stirring and the precipitated product was filtered off with suction. To give 4.3 g (yield 57%) of yellow product which was recrystallized from toluene. MS (m/z, $FAB^+$):664.3

EXAMPLE 2

Synthesis of EX12

Synthesis of 2-(biphenyl-2-yl)-7-bromo-9,9-dimethyl-9H-fluorene

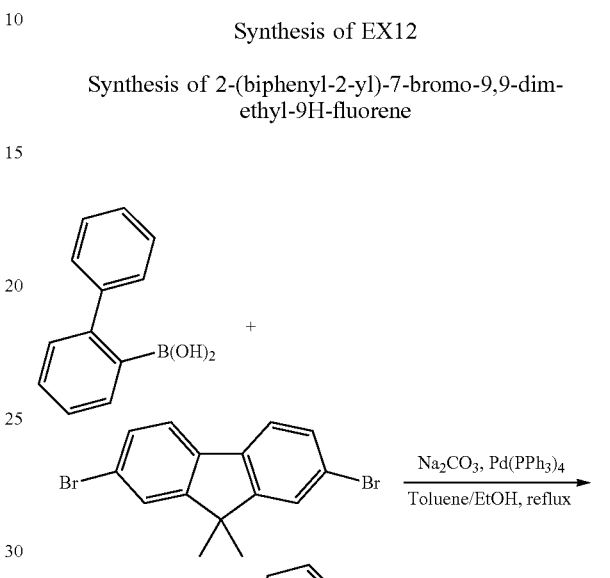

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of $Pd(PPh_3)_4$, 75 ml of 2M $Na_2CO_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 12-bromo-10,10-dimethyl-10H-indeno[2,1-b]triphenylene

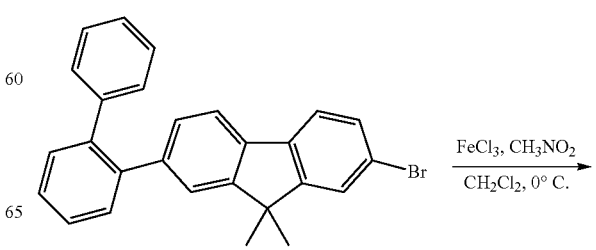

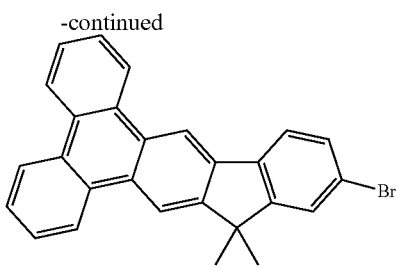

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron(III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). $^1$H NMR (CDCl$_3$, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of 3-chloro-N-(10,10-dimethyl-10H-indeno[2,1-b]triphenylen-12-yl)pyridin-2-amine

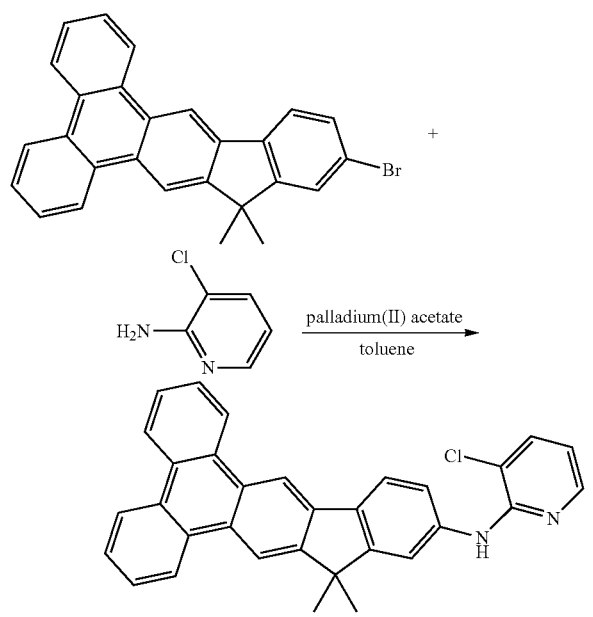

A mixture of 10.7 g (25.3 mmol) of 12-bromo-10,10-dimethyl-10H-indeno-[1,2-b]triphenylene, 3.3 g (25.4 mmol) of 3-chloropyridin-2-amine, 0.11 g (0.5 mmol) of palladium(II)acetate, 0.55 g (1.0 mmol) of 1,1-bis(diphenylphosphino)ferrocene, 4.85 g (50.6 mmol) of sodium tort-butoxide and 100 ml toluene was degassed and placed under nitrogen, and then heated at 110° C. for overnight. After finishing the reaction, the mixture was allowed to cool to room temperature. The organic phase separated and washed with ethyl acetate and water. After drying over magnesium sulfate, the solvent was removed in vacuo. The residue was purified by column chromatography on silica gel (hexane-dichloromethane) to give product (6.9 g, 14.7 mmol, 58%) as a light-yellow solid.

Synthesis of Intermediate II

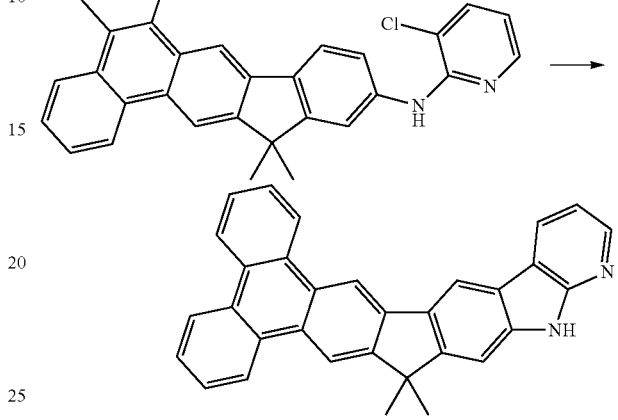

intermediate II

A mixture of 6.9 g (14.7 mmol) of 3-chloro-N-(10,10-dimethyl-10H-indeno[2,1-b]triphenylen-12-yl)pyridin-2-amine, 0.4 g (1.6 mmol) of palladium(II) acetate, 70 ml of pivalic acid, 0.72 g of potassium carbonate (6 mmol) and 210 ml 1-methyl-2-pyrrolidone was degassed and placed under nitrogen, and then heated at 130° C. for 24 hours. After finishing the reaction, the mixture was allowed to cool to room temperature. The organic layer was extracted with dichloromethane and water, dried with anhydrous magnesium sulfate, the solvent was removed and the residue was recrystallized from hexane and dichloromethane to give product 4.9 g (yield 76%).

Synthesis of EX12

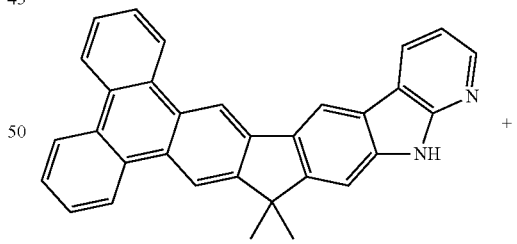

intermediate II

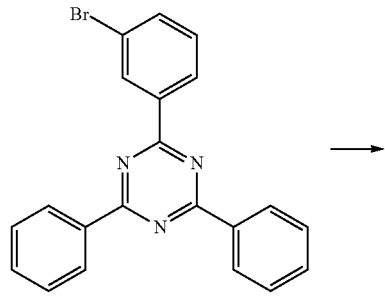

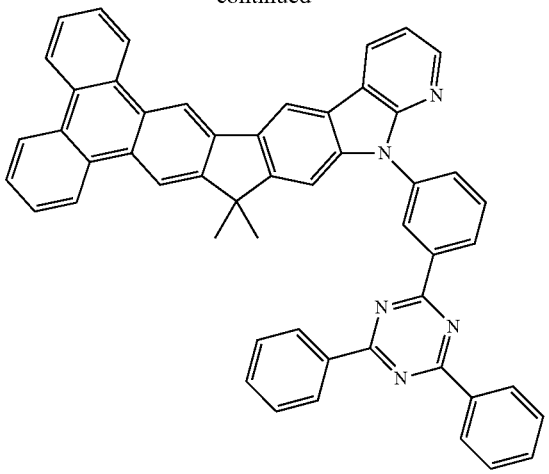

A mixture of 4.9 g (11.3 mmol) intermediate II, 5.4 g (14 mmol) of 2-(3-bromophenyl)-4,6-diphenyl-1,3,5-triazine, 0.05 g (0.2 mmol) of palladium (II)acetate, 0.15 g (0.4 mmol) of 2-(dicyclohexylphosphino)biphenyl, 2 g (20 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give 4.4 g (yield 53%) of product which was recrystallized from toluene. MS (m/z, FAB$^+$):741.4

EXAMPLE 3

Synthesis of EX16

Synthesis of 2-(10,10-dimethyl-10H-indeno[2,1-b]triphenylen-12-yl)-4,4,5,5-tetramethyl-1,3,2-dioxaborolane

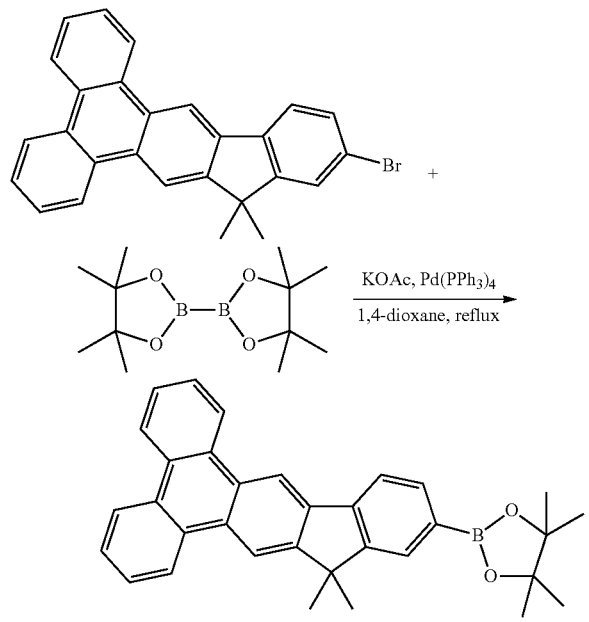

A mixture of 10.7 g (25.3 mmol) of 12-bromo-10,10-dimethyl-10H-indeno-[1,2-b]triphenylene, 7.7 g (30.3 mmol) of bis(pinacolato)diboron, 0.3 g (0.26 mmol) of Pd(PPh$_3$)$_4$, 7.4 g (75.4 mmol) of potassium acetate, and 300 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (9.5 g, 20.2 mmol, 80%) as a light-yellow solid; $^1$H NMR (CDCl3, 400 MHz): chemical shift (ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

Synthesis of 3-(10,10-dimethyl-10H-indeno[2,1-b]triphenylen-12-yl)-4-nitropyridine

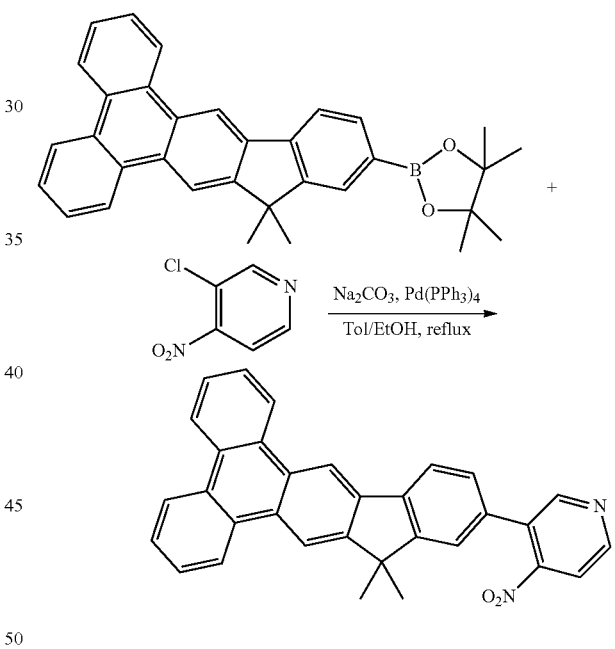

A mixture of 9.5 g (20.2 mmol) of 2-(10,10-dimethyl-10H-indeno[2,1-b]triphenylen-12-yl)-4,4,5,5-tetramethyl-1,3,2-dioxaborolane, 3.5 g (22 mmol) of 3-chloro-4-nitropyridine, 0.44 g (0.4 mmol) of tetrakis(triphenyl phosphine) palladium, 30 ml of 2M Na$_2$CO$_3$, 40 ml of EtOH and 80 ml toluene was degassed and placed under nitrogen, and then heated at 90° C. overnight. After finishing the reaction, the mixture was allowed to cool to room temperature. The solution was extracted with 250 ml of ethyl acetate and 1000 ml of water. The organic layer was dried with anhydrous magnesium sulfate and the solvent was evaporated under reduced pressure. The residue was purified by column chromatography on silica (hexane-dichloromethane) to give product 6.3 g (67%).

Synthesis of Intermediate III

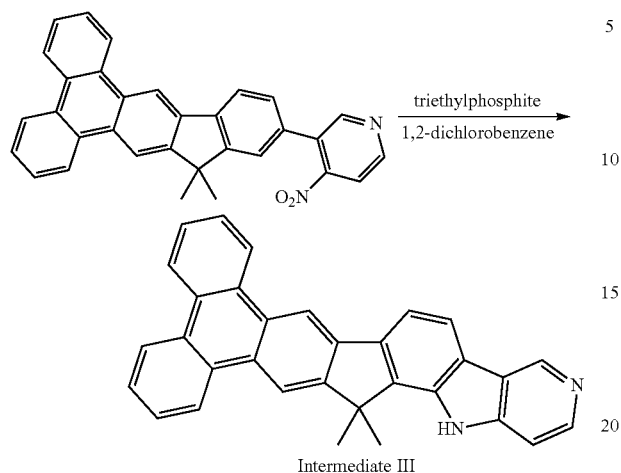

Intermediate III

A mixture of 5.5 g (11.8 mmol) of 3-(10,10-dimethyl-10H-indeno[2,1-b]triphenylen-12-yl)-4-nitropyridine, 30 ml of triethylphosphite, 15 ml of 1,2-dichlorobenzene, was placed under nitrogen, and then heated at 160° C. overnight. After finishing the reaction, the mixture was allowed to cool to room temperature. Than 200 ml of MeOH was added, while stirring and the precipitated product was filtered off with suction. To give 2.4 g (yield 47%) of yellow product which was purified by column chromatography on silica gel (Hx~CH$_2$Cl$_2$).

Synthesis of Intermediate IV

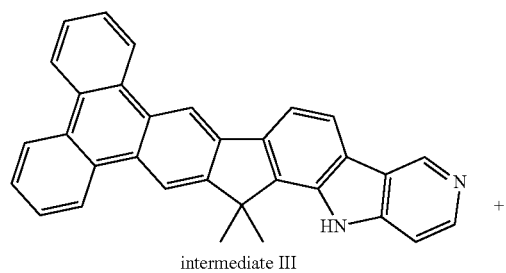

intermediate III

+ intermediate IV

A mixture of 2.47 g (5.5 mmole) intermediate III, 1.9 g (6.6 mmole) of 1-bromo-3-iodobenzene, 5.7 g (30 mmole) of copper(I)iodide, 6.3 g (30 mmole) of potassium phosphate, 3.4 g (30 mmole) of trans-1,2-cyclohexanediamine and 1,4-dioxane 100 ml were refluxed under nitrogen for about overnight. Then, the solution was filtered at 110° C. To receive the filtrate, the 1,4-dioxane was removed under reduced pressure from the filtrate. The filtrate was extracted with 50 ml dichloromethane and 200 ml water, the organic layer was dried with anhydrous magnesium sulfate, the solvent was removed and the residue was purified by column chromatography on silica gel (hexane-ethyl acetate) to give product 2.1 g (64%).

Synthesis of Intermediate V

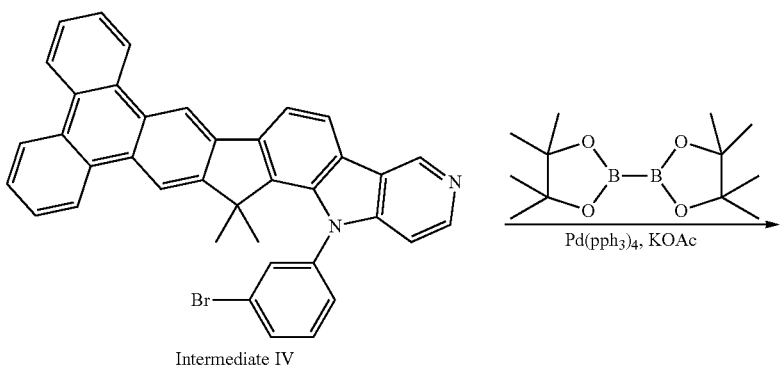

Intermediate IV

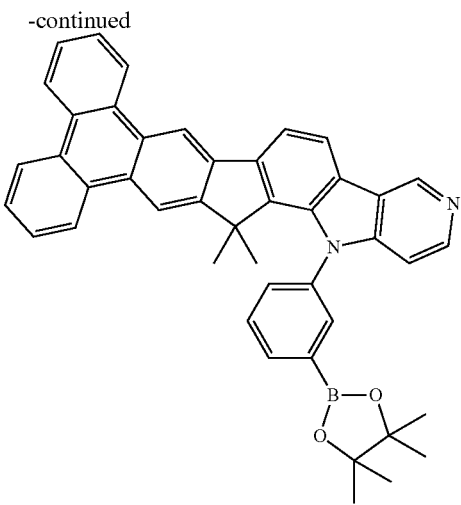

Intermediate V

A mixture of 2.1 g (3.56 mmol) of intermediate IV, 1.8 g (7.1 mmol) of bis(pinacolato)diboron, 0.24 (0.2 mmol) of tetrakis(triphenylphosphine) palladium, 2.1 g (20.6 mmol) of potassium acetate, and 50 ml of 1,4-dioxane was degassed and placed under nitrogen, and then heated at 90° C. for 24 h. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 1.5 g of light yellow product (yield 67%).

Synthesis of EX16

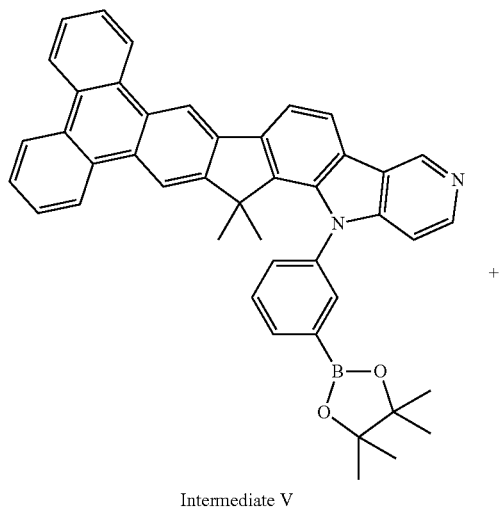

Intermediate V

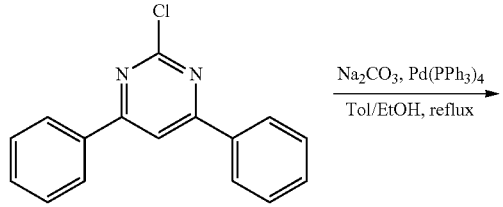

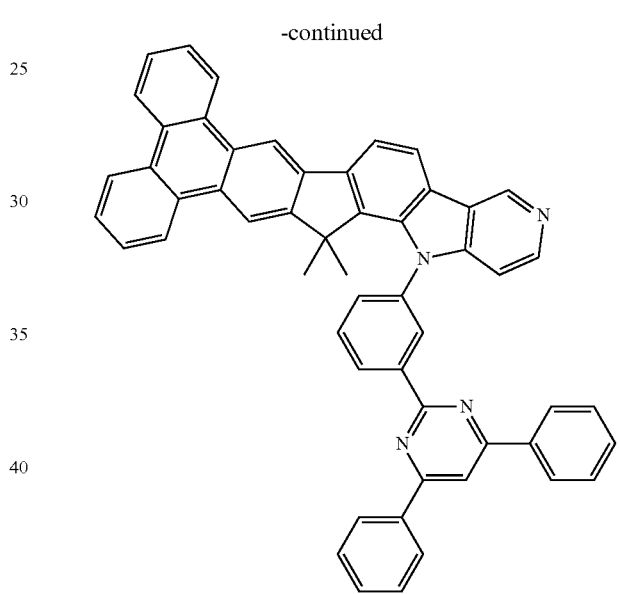

A mixture of 1.5 g (2.36 mmol) of intermediate V, 0.95 g (3.5 mmol) of 2-chloro-4,6-diphenyl-1,3,5-triazine, 0.12 g (0.1 mmol) of tetrakis (triphenylphosphine)palladium, 5 ml of 2M $Na_2CO_3$, 10 ml of EtOH and 20 ml toluene was degassed and placed under nitrogen, then heated at 110° C. overnight. After finishing the reaction, the mixture was allowed to cool to room temperature. Than 100 ml of MeOH was added, while stirring and the precipitated product was filtered off with suction. To give 1 g (yield 61%) of yellow product which was recrystallized from toluene. MS (m/z, $FAB^+$):740.4

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N,N-Bis(naphthalene-1-yl)-N,N-bis(phenyl)-benzidine (NPB) is most widely used as the hole transporting layer, N-(biphenyl-4-yl)-9,9-dimethyl-N-(4'-phenylbiphenyl-4-yl)-9H-fluoren-2-amine (EB2) is used as electron blocking layer, H1 and H2 are used as phosphorescent host for comparable with the present invention of EX7, EX12 and EX16. The chemical structure shown below:

HAT-CN

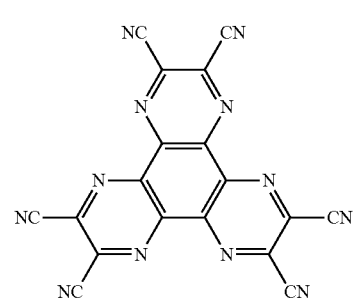

NPB

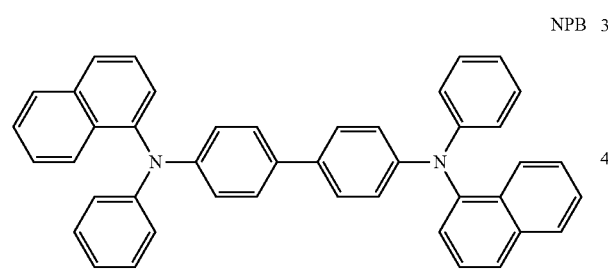

EB2

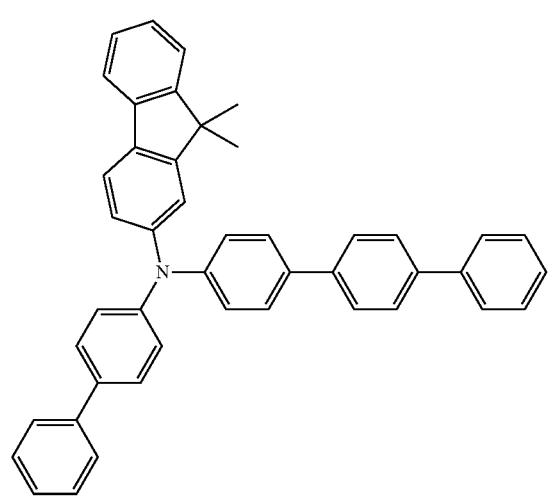

H1

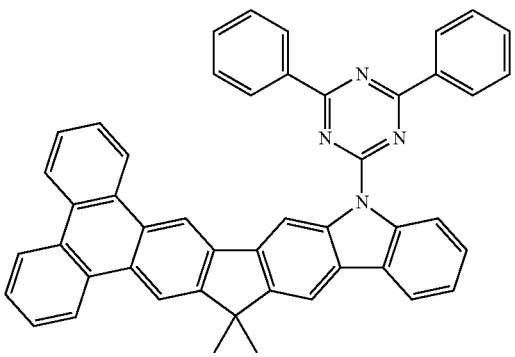

H2

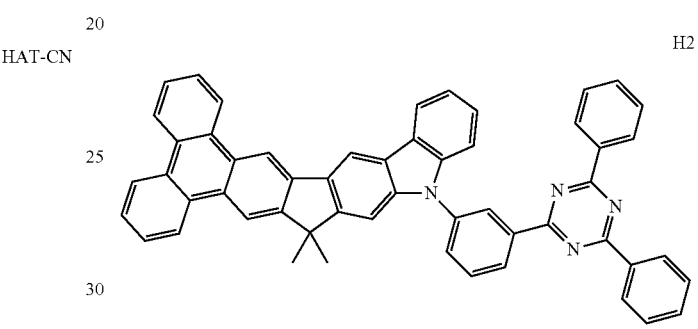

EX7

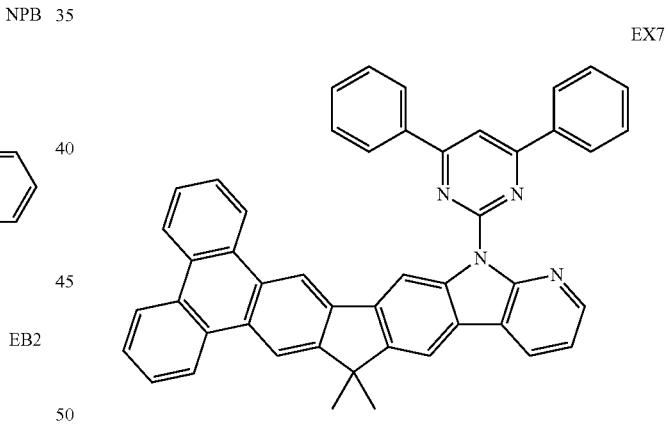

EX12

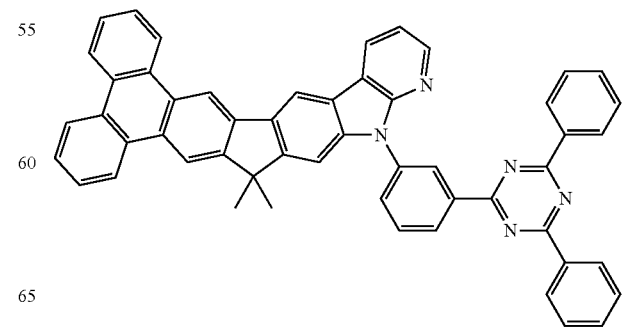

EX16

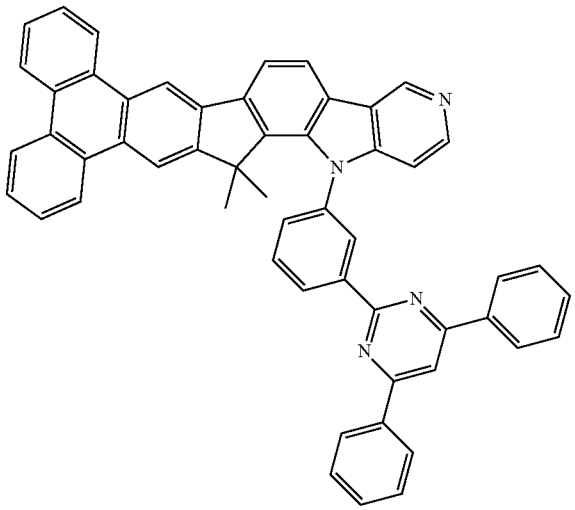

Organic iridium complexes are widely used as phosphorescent dopant for light emitting layer, Ir(ppy)₃, Ir(piq)₂(acac) and Ir(2-phq)₂(acac) are widely used for phosphorescent dopant of light emitting layer for organic EL device.

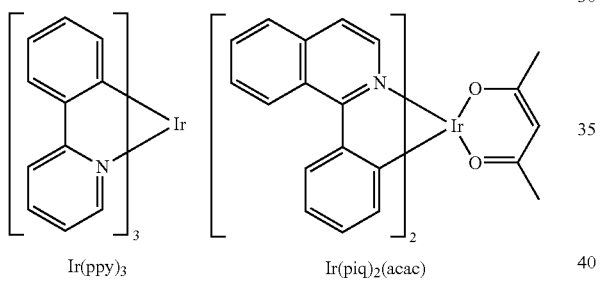

Ir(ppy)₃    Ir(piq)₂(acac)

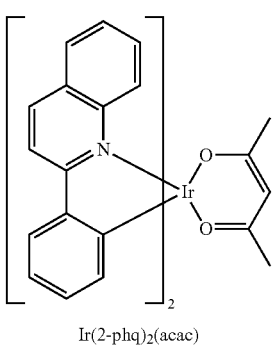

Ir(2-phq)₂(acac)

HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

LiQ

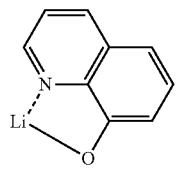

ET2

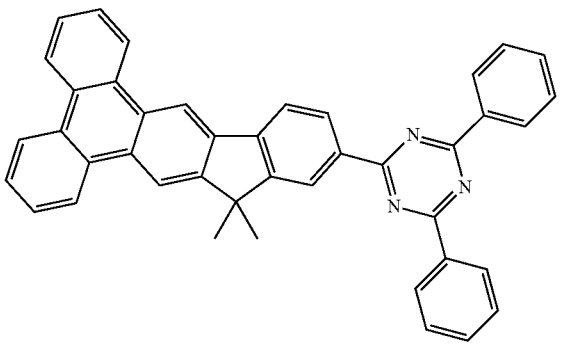

HB3

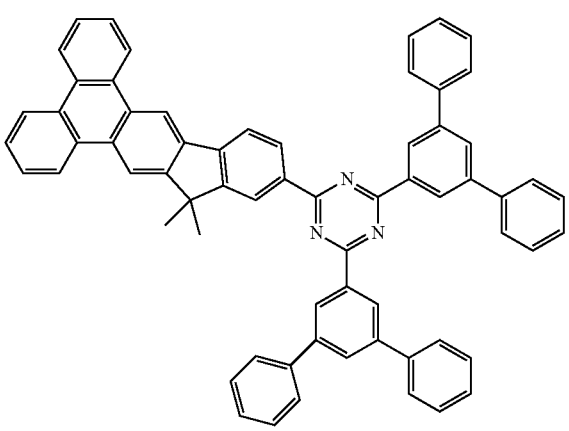

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li₂O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 4

Using a procedure analogous to the above mentioned general method, phosphorescent emitting organic EL device having the following device structure was produced (See FIG. 1). Device:ITO/HAT-CN (20 nm)/NPB (110 nm)/EB2 (5 nm)/phosphorescent emitting host doped 15% phosphorescent emitting dopant (30 nm)/HB3 (10 nm)/ET2 doped 40% LiQ (35 nm)/LiQ (1 nm)/Al (160 nm). The I-V-B (at 1000 nits) and half-life time of phosphorescent emitting organic EL device testing report as Table 1. The half-life time is defined that the initial luminance of 3000 cd/m² has dropped to half.

TABLE 1

| Emitting host | Emitting dopant | Voltage (V) | Efficiency (cd/A) | Color | Half-life time (hour) |
|---|---|---|---|---|---|
| H1 | Ir(ppy)$_3$ | 3.5 | 43 | green | 680 |
| H2 | Ir(ppy)$_3$ | 3.7 | 50 | green | 650 |
| EX7 | Ir(ppy)$_3$ | 3.5 | 48 | green | 700 |
| EX12 | Ir(ppy)$_3$ | 3.6 | 53 | green | 600 |
| EX16 | Ir(ppy)$_3$ | 3.2 | 56 | green | 900 |
| H2 | Ir(piq)$_2$(acac) | 4.0 | 21 | Red | 350 |
| EX7 | Ir(piq)$_2$(acac) | 3.5 | 16 | Red | 330 |
| EX12 | Ir(piq)$_2$(acac) | 3.5 | 26 | Red | 400 |
| EX16 | Ir(piq)$_2$(acac) | 3.6 | 31 | Red | 370 |
| H2 | Ir(2-phq)$_2$(acac) | 4.6 | 18 | Orange | 500 |
| EX12 | Ir(2-phq)$_2$(acac) | 4.5 | 30 | Orange | 650 |
| EX16 | Ir(2-phq)$_2$(acac) | 4.9 | 32 | Orange | 680 |

In the above preferred embodiments for phosphorescent organic EL device testing report (see Table 1), we show that the triphenylene-based fused carbazole compound with a general formula (1) or formula (2) used as phosphorescent light emitting host of emitting layer for organic EL device in the present invention display good performance than the prior art of organic EL materials (H1 and H2). More specifically, the organic EL device in the triphenylene-based fused carbazole compound in the present invention use the general formula (1) or formula (2) as phosphorescent light emitting host material to collocate with ET2 and HB3 shown lower power consumption, longer half-life time and higher efficiency.

To sum up, the present invention discloses an triphenylene-based fused carbazole compound which can be used as phosphorescent light emitting host of emitting layer or a thermally activated delayed fluorescence (TADF) material of emitting layer. The mentioned the triphenylene-based fused carbazole compound represented by the following formula (1) or formula (2):

wherein L represents a single bond, a substituted or unsubstituted arylene group having 6 to 30 ring carbon atoms, or a substituted or unsubstituted heterarylene group having 3 to 30 ring carbon atoms, Ar is selected from the group consisting of a substituted or unsubstituted aryl group having 6 to 60 carbon atoms or a substituted or unsubstituted heteroaryl group having 3 to 60 carbon atoms, preferably Ar represents a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $X_1$ to $X_4$ independently represent a nitrogen atom or $C(R_s)$, and each $R_s$ represents a hydrogen, a halide and a substituent, $R_1$ to $R_3$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. A compound with a general formula (1) or formula (2) as follows:

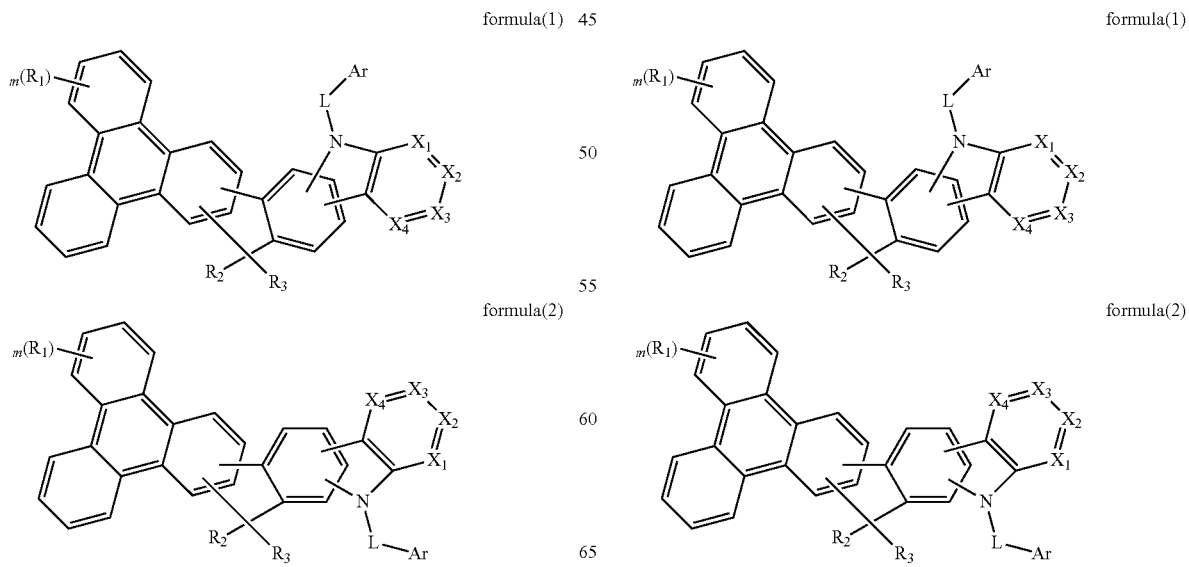

wherein L represents a substituted or unsubstituted arylene group having 6 to 30 ring carbon atoms, or a substituted or unsubstituted heterarylene group having 3 to 30 ring carbon atoms, Ar is selected from the group consisting of a substituted or unsubstituted aryl group having 6 to 60 carbon atoms, preferably Ar represents a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $X_1$ to $X_4$ independently represent a nitrogen atom or $C(R_s)$, and each $R_s$ represents a hydrogen, a halide and a substituent, $R_1$ to $R_3$ are independently selected from the group consisting of a halide, a substituted or unsubstituted aralkyl group having 6 to 30 carbon atoms, a substituted or unsubstituted heteroaryl group having 3 to 30 carbon atoms; and where m is 1-4.

2. The compound according to claim 1, wherein the L is represented by the following formula (3):

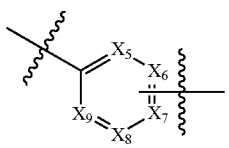

formula(3)

wherein $X_5$ independently represent a $C(R_s)$, and each $R_s$ represents a hydrogen or a substituent, wherein $X_6$ independently represent a nitrogen atom or $C(R_s)$, and each $R_s$ represents a phenyl or a substituent, wherein $X_7$ independently represent a nitrogen atom or $C(R_s)$, and each $R_s$ represents a hydrogen or a substituent, $X_8$ independently represent a nitrogen atom or $C(R_s)$, and each $R_s$ represents a hydrogen, a phenyl or a substituent, wherein $X_9$ independently represent a $C(R_s)$, and each $R_s$ represents a hydrogen, a phenyl or a substituent.

3. The compound according to claim 1, wherein the compound formula (1) or formula (2) are represented by the following formula (4) to formula (21):

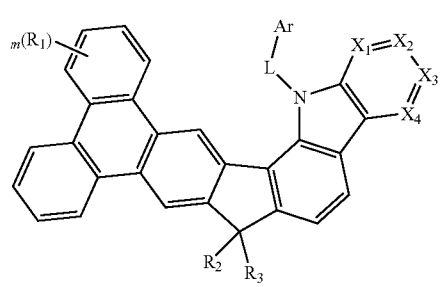

formula(4)

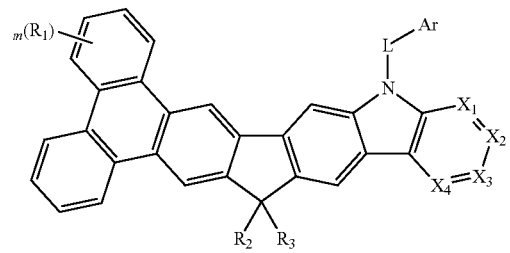

formula(5)

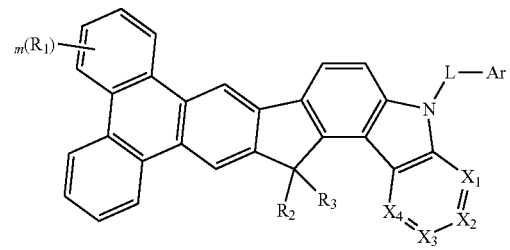

formula(6)

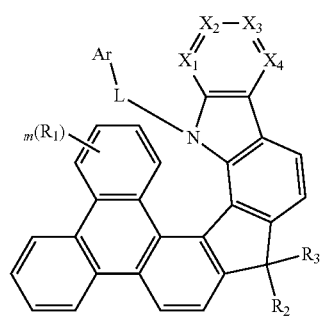

formula(7)

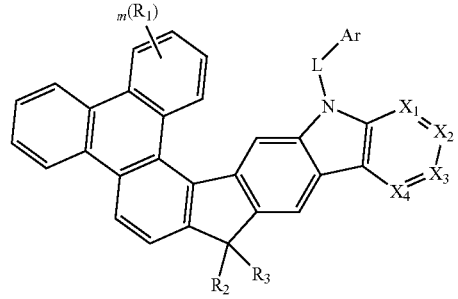

formula(8)

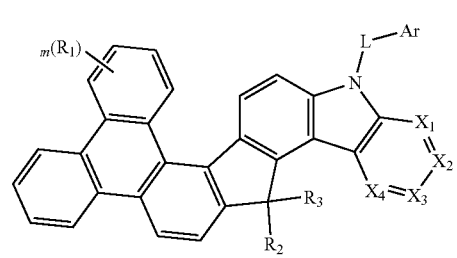

formula(9)

formula(10)
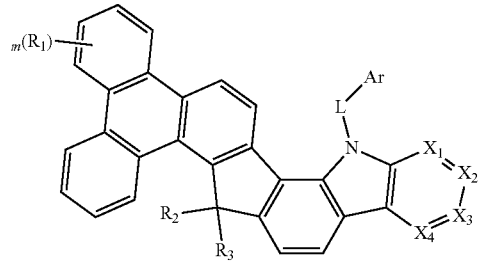
formula(11)
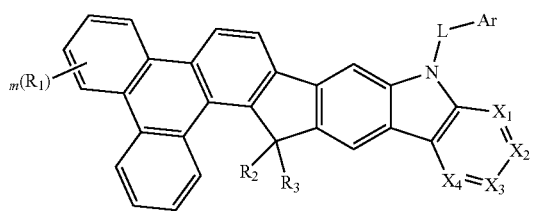
formula(12)
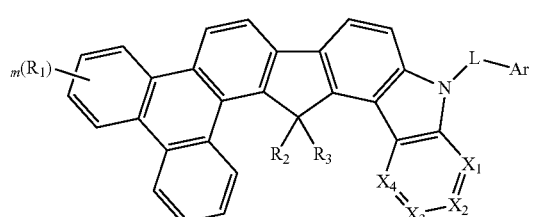
formula(13)
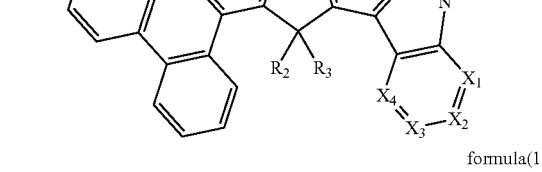
formula(14)
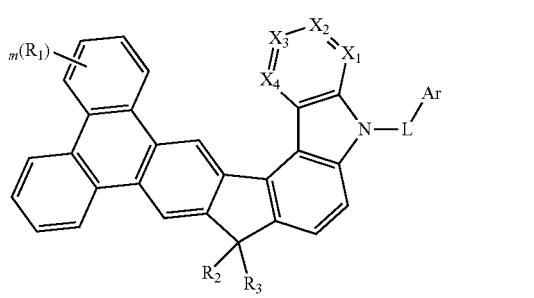
formula(15)
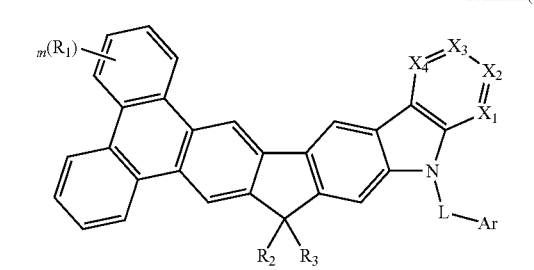
formula(16)
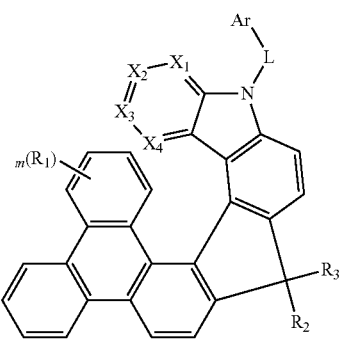
formula(17)
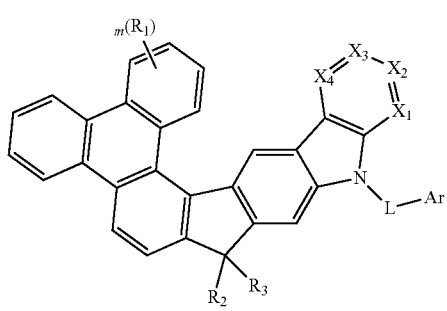
formula(18)
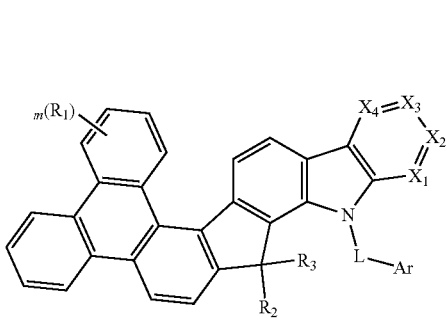
formula(19)
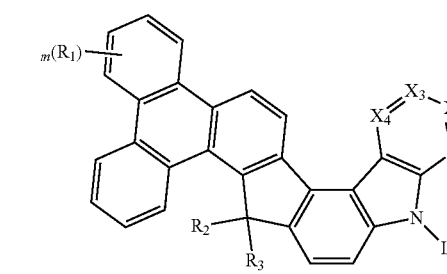
formula(20)
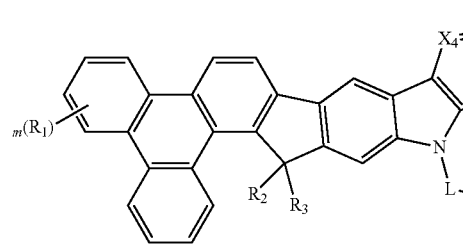

-continued

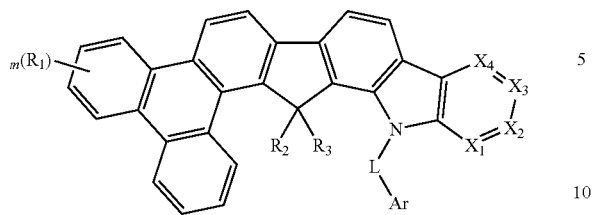

formula(21)

wherein L represents a substituted or unsubstituted arylene group having 6 to 30 ring carbon atoms, or a substituted or unsubstituted heterarylene group having 3 to 30 ring carbon atoms, Ar is selected from the group consisting of a substituted or unsubstituted aryl group having 6 to 60 carbon atoms, preferably Ar represents a substituted or unsubstituted phenyl group, a substituted or unsubstituted naphthyl group, a substituted or unsubstituted biphenyl group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group; $X_1$ to $X_4$ independently represent a nitrogen atom or $C(R_s)$, and each $R_s$ represents a hydrogen, a halide and a substituted, $R_1$ to $R_3$ are independently selected from the group consisting of a halide, a substituted or unsubstituted aralkyl group having 6 to 30 carbon atoms, a substituted or unsubstituted heteroaryl group having 3 to 30 carbon atoms: wherein m is 1-4.

4. The compound according to claim 3, wherein the L is represented by the following formula (3):

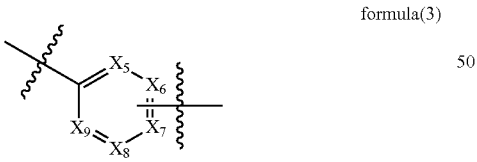

formula(3)

wherein $X_5$ independently represent a $C(R_s)$, and each $R_s$ represents a hydrogen, or a substituent, $X_6$ independently represent a nitrogen atom or $C(R_s)$, and each $R_s$ represents a phenyl or a substituent, wherein $X_7$ independently represent a nitrogen atom or $C(R_s)$, and each $R_s$ represents a hydrogen or a substituent, $X_8$ independently represent a nitrogen atom or $C(R_s)$, and each $R_s$ represents a hydrogen, a phenyl or a substituent, wherein X, independently represent a $C(R_s)$, and each $R_s$ represents a hydrogen, a phenyl or a substituent.

5. The compound according to claim 3, wherein the Ar is consisting of group represented as follows:

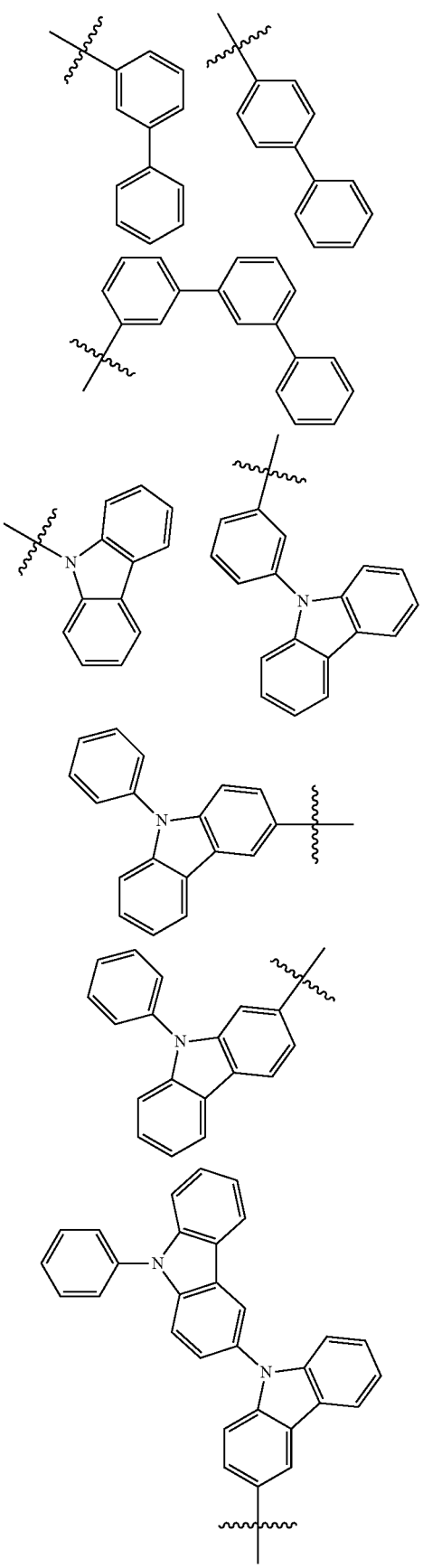

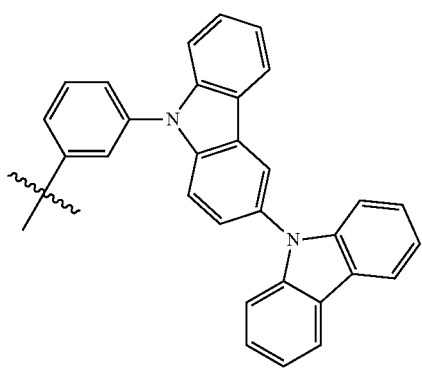
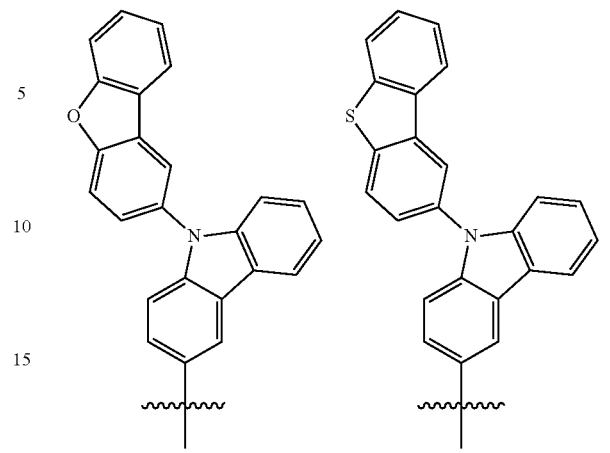
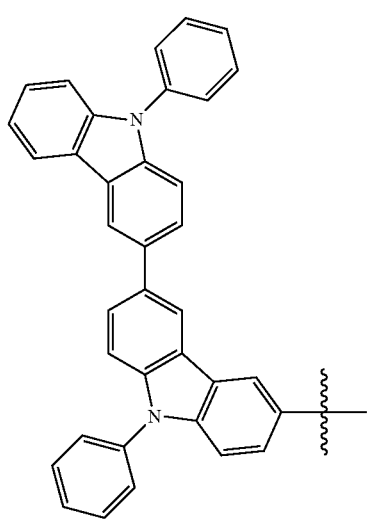
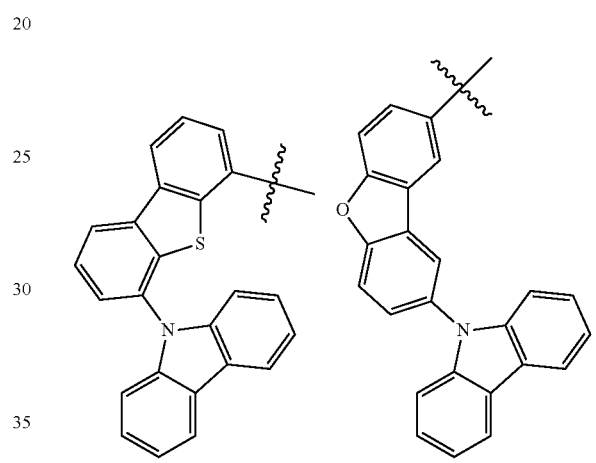
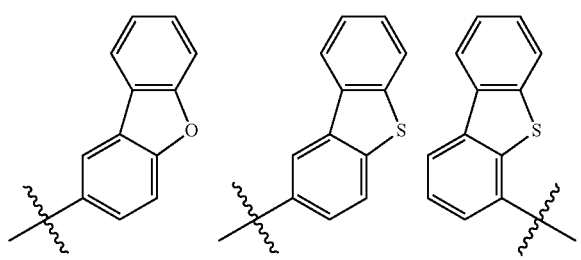
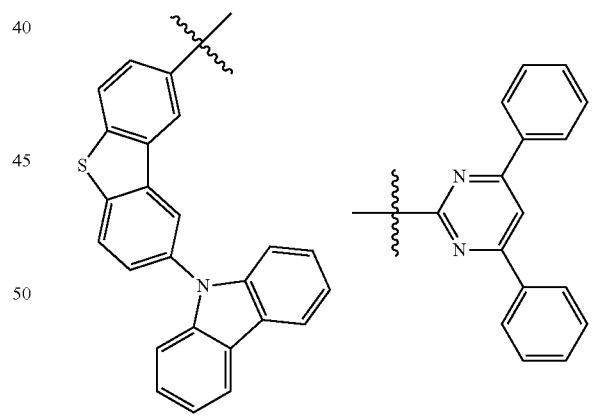
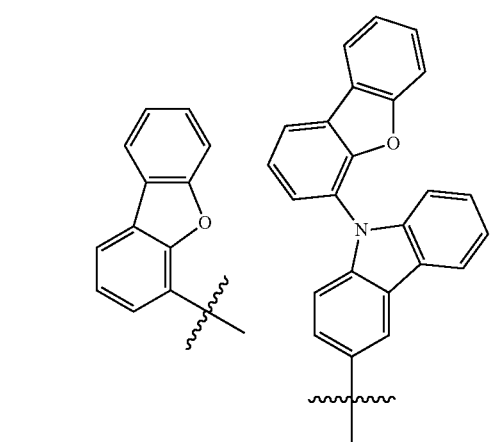

-continued
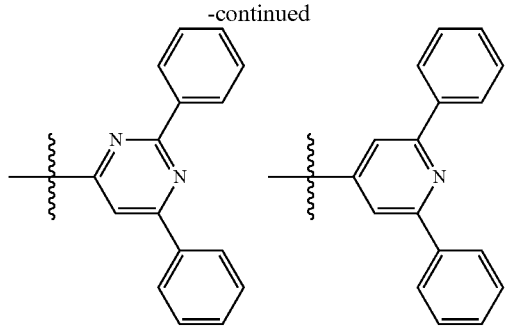
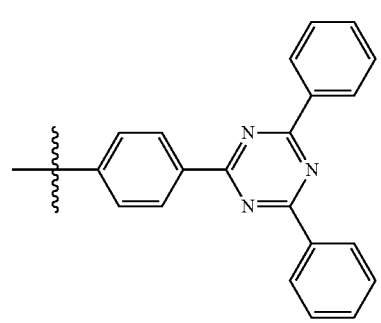
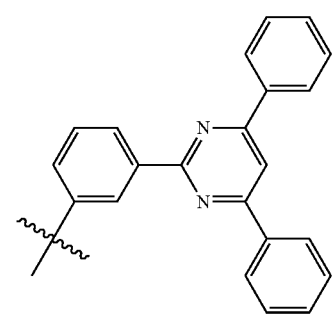
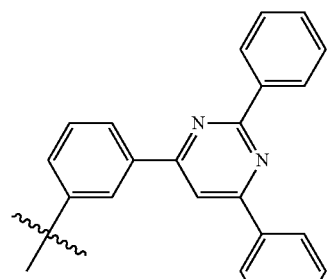
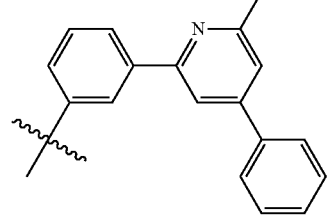
-continued
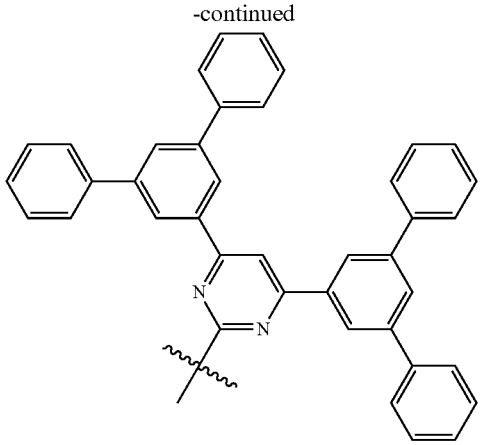
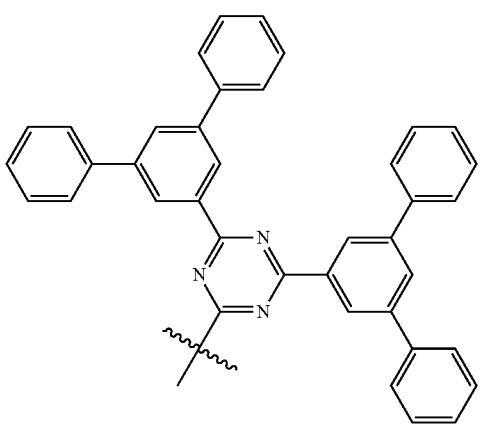
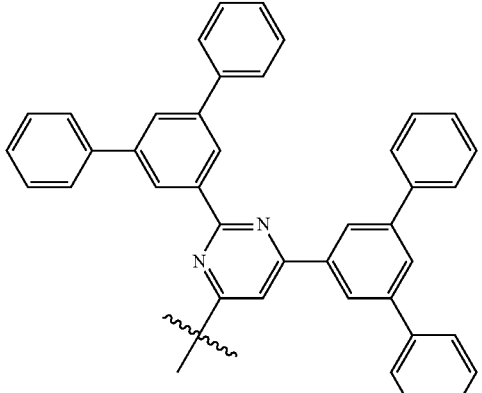
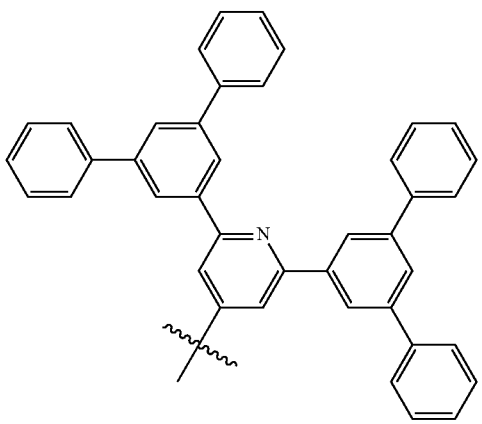

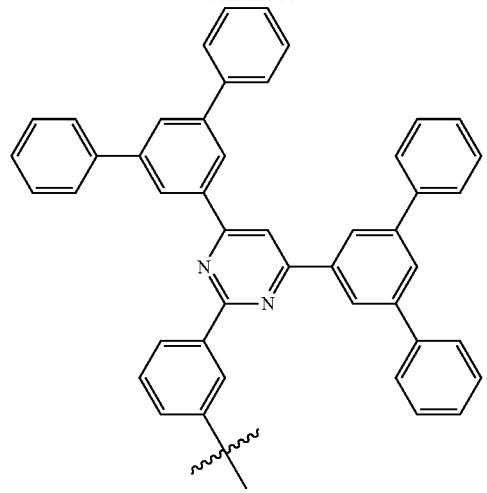
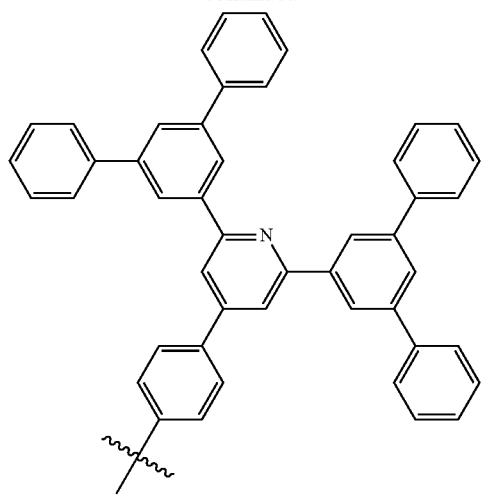
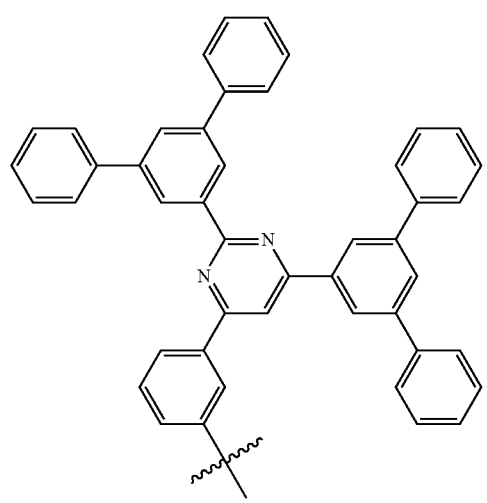
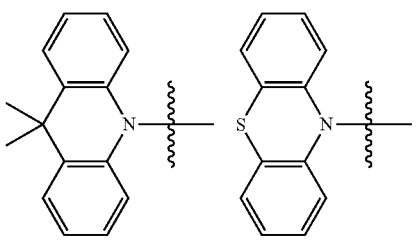
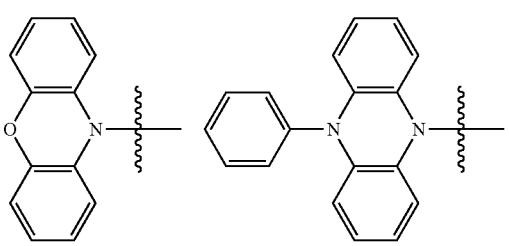
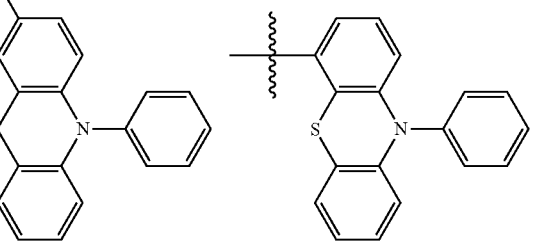
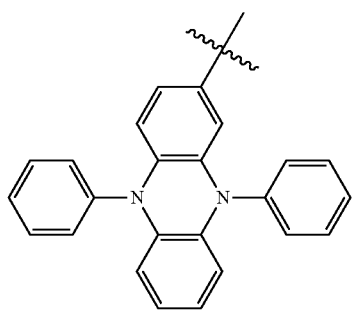

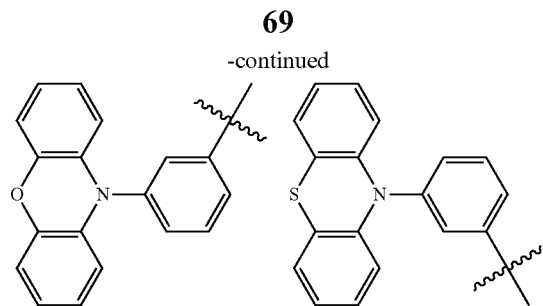

6. A organic electroluminescence device comprising a pair of electrodes consisting of a cathode and an anode, and between the pairs of electrodes comprising at least a light emitting layer, one or more layers of organic thin film layer, wherein at least the light emitting layer comprising the compound with a general formula (1) or formula (2) according to claim 1.

7. The organic electroluminescence device according to claim 6, wherein the light emitting layer comprising the compound with a general formula (1) or formula (2) is a phosphorescent host material.

8. The organic electroluminescence device according to claim 6, wherein the emitting layer comprising the compound with a general formula (1) or formula (2) is a thermally activated delayed fluorescence host material.

9. The organic electroluminescence device according to claim 6, wherein the emitting layer comprising the compound with a general formula (1) or formula (2) is a thermally activated delayed fluorescence dopant material.

10. The organic electroluminescence device according to claim 6, wherein the light emitting layer comprising phosphorescent dopant material.

11. The organic electroluminescent device according to claim 10, wherein the phosphorescent dopant are iridium complexes.

12. The organic electroluminescent device according to claim 6, wherein the light emitting layer comprising compounds as the following formulas:

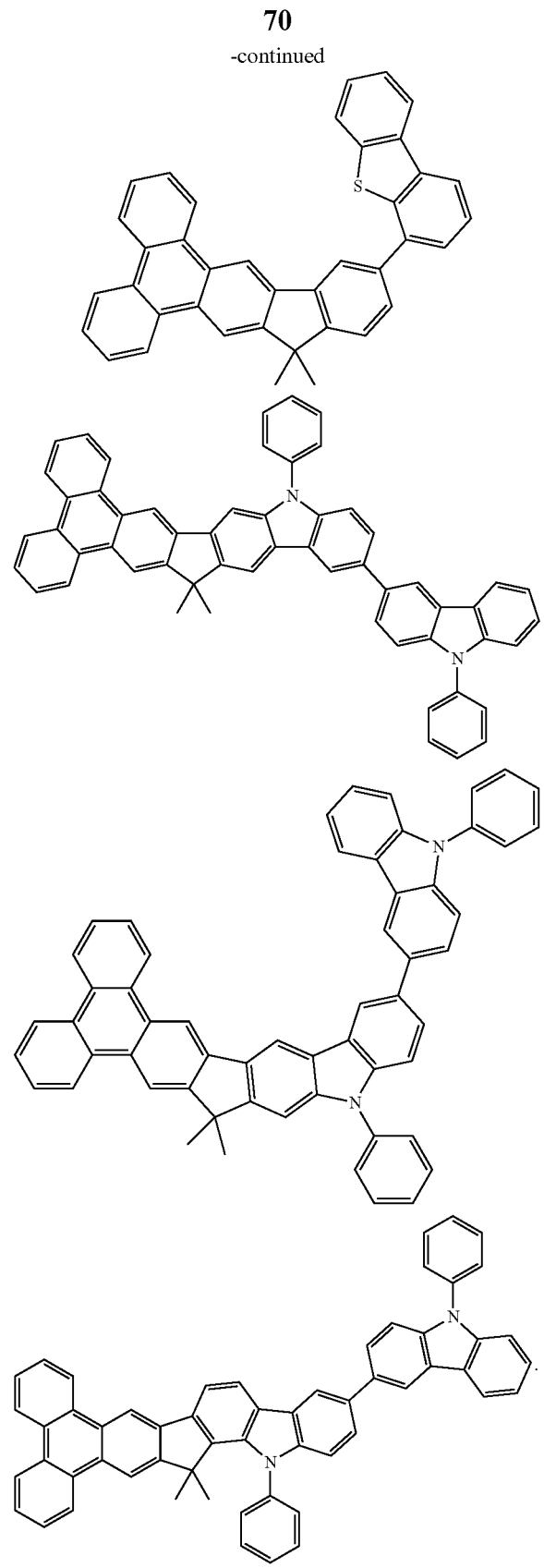

13. The organic electroluminescent device according to claim 6, wherein the electron transport layer or hole blocking layer comprising compound as the following formulas:

-continued

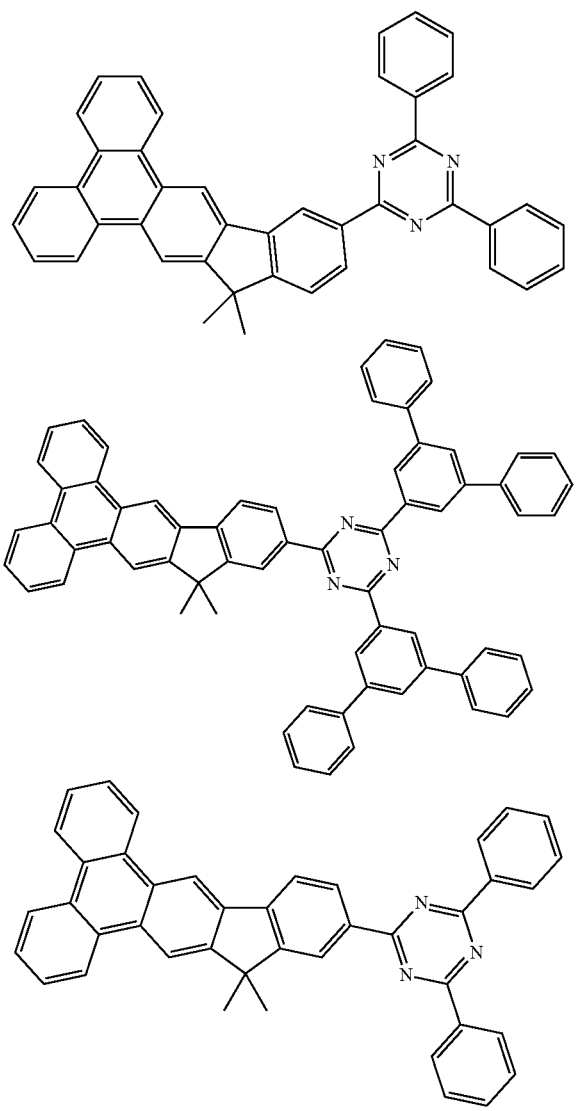
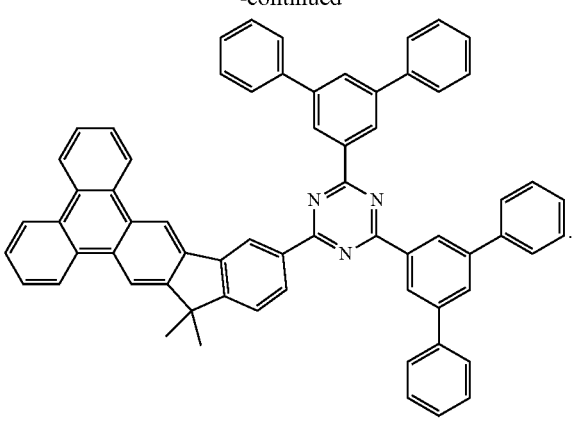

14. The organic electroluminescence device according to claim 13, wherein the electron transport layer comprising lithium or 8-hydroxyuinolinolato-lithium.

15. The organic electroluminescence device according to claim 6, wherein the light emitting layer emits phosphorescent red, blue, green and yellow lights.

16. The organic electroluminescence device according to claim 6, wherein the light emitting layer emits thermally activated delayed fluorescent red, blue, green and yellow lights.

17. The organic electroluminescence device according to claim 6, wherein the device is an organic light emitting device.

18. The organic electroluminescent device according to claim 6, wherein the device is a lighting panel.

19. The organic electroluminescent device according to claim 6, wherein the device is a backlight panel.

* * * * *